United States Patent
Kim et al.

(10) Patent No.: US 9,837,623 B2
(45) Date of Patent: Dec. 5, 2017

(54) COMPOUND, ORGANIC OPTOELECTRONIC DEVICE COMPRISING THE SAME, AND DISPLAY DEVICE

(71) Applicant: SAMSUNG SDI CO., LTD., Yongin-si, Gyeonggi-do (KR)

(72) Inventors: Hyun-Jung Kim, Suwon-si (KR); Mi-Young Chae, Suwon-si (KR); Nam-Heon Lee, Suwon-si (KR); Dal-Ho Huh, Suwon-si (KR); Wook Kim, Suwon-si (KR); Youn-Hwan Kim, Suwon-si (KR); Jun-Seok Kim, Suwon-si (KR); Sang-Il Lee, Suwon-si (KR); Hyun Gyu Lee, Suwon-si (KR); Chun-Keun Jang, Suwon-si (KR); Ju-Yeon Jung, Suwon-si (KR)

(73) Assignee: SAMSUNG SDI CO., LTD., Yongin-Si, Gyeonggi-Do (KR)

( * ) Notice: Subject to any disclaimer, the term of this patent is extended or adjusted under 35 U.S.C. 154(b) by 81 days.

(21) Appl. No.: 15/021,342

(22) PCT Filed: Jul. 17, 2014

(86) PCT No.: PCT/KR2014/006507
§ 371 (c)(1),
(2) Date: Mar. 11, 2016

(87) PCT Pub. No.: WO2015/088118
PCT Pub. Date: Jun. 18, 2015

(65) Prior Publication Data
US 2016/0226007 A1    Aug. 4, 2016

(30) Foreign Application Priority Data
Dec. 9, 2013 (KR) .......................... 10-2013-0152495

(51) Int. Cl.
H01L 51/00 (2006.01)
C09K 11/06 (2006.01)
H01L 51/50 (2006.01)
C07F 15/00 (2006.01)

(52) U.S. Cl.
CPC ...... *H01L 51/0085* (2013.01); *C07F 15/0033* (2013.01); *C09K 11/06* (2013.01); *H01L 51/0086* (2013.01); *H01L 51/0087* (2013.01); *H01L 51/0088* (2013.01); *H01L 51/50* (2013.01); *C09K 2211/185* (2013.01); *H01L 51/008* (2013.01)

(58) Field of Classification Search
CPC ............ H01L 51/0085; H01L 51/0087; H01L 51/0086; H01L 51/0088; H01L 51/50; H01L 51/008; C07F 15/0033; C09K 11/06; C09K 2211/185
See application file for complete search history.

(56) References Cited

U.S. PATENT DOCUMENTS

2013/0112921 A1    5/2013 Stoessel et al.
2015/0270500 A1*   9/2015 Stoessel ............. H01L 51/0094
                                           252/301.35

FOREIGN PATENT DOCUMENTS

| | | |
|---|---|---|
| JP | WO2007/088768 A1 | 8/2007 |
| JP | 2010-219275 A | 9/2010 |
| JP | 2010-272727 A | 12/2010 |
| JP | 2011-068848 A | 4/2011 |
| JP | 2012-516831 A | 7/2012 |
| JP | 2013-507404 A | 3/2013 |
| JP | 2013-531652 A | 8/2013 |
| KR | 10-2005-0015811 A | 2/2005 |
| WO | WO 2007/029461 A1 | 3/2007 |
| WO | WO 2007/088768 A1 | 8/2007 |
| WO | WO 2011/134013 A1 | 11/2011 |

OTHER PUBLICATIONS

International Search Report for PCT/KR2014/006507.

* cited by examiner

*Primary Examiner* — Alexander Kollias
(74) *Attorney, Agent, or Firm* — Lee & Morse, P.C.

(57) ABSTRACT

A compound represented by Chemical Formula 1, an organic optoelectronic device including the same, and a display device including the organic optoelectronic device are provided. The structure of the compound represented by Chemical Formula 1 is described in the present specification.

10 Claims, 1 Drawing Sheet

COMPOUND, ORGANIC OPTOELECTRONIC DEVICE COMPRISING THE SAME, AND DISPLAY DEVICE

CROSS REFERENCE TO RELATED APPLICATIONS

This is the U.S. national phase application based on PCT Application No. PCT/KR2014/006507, filed Jul. 17, 2014, which is based on Korean Patent Application No. 10-2013-0152495, filed Dec. 9, 2013, the entire contents of all of which are hereby incorporated by reference.

TECHNICAL FIELD

A compound, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectronic device include an organic photoelectric device, an organic light emitting diode, an organic solar cell, and an organic photo-conductor drum, and the like.

Among them, the organic light emitting diode (OLED) has recently drawn attention due to an increase in demand for flat panel displays. The organic light emitting diode converts electrical energy into light by applying current to an organic light emitting material, and has a structure in which an organic is interposed between an anode and a cathode. Herein, the organic layer may include an emission layer and optionally an auxiliary layer, and the auxiliary layer may include at least one layer selected from, for example a hole injection layer, a hole transport layer, an electron blocking layer, an electron transport layer, an electron injection layer, and a hole blocking layer in order to improve efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

A compound capable of providing an organic optoelectronic device having characteristics such as high efficiency, a long life-span, thermal stability, and the like is provided.

An organic optoelectronic device including the compound and a display device are provided.

Technical Solution

In one embodiment of the present invention, a compound represented by Chemical Formula 1 is provided.

[Chemical Formula 1]

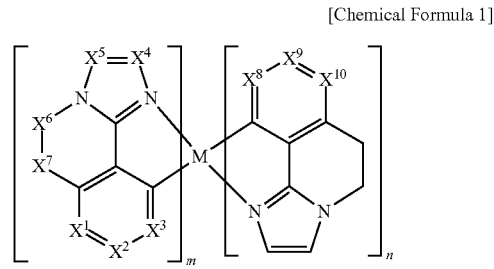

In Chemical Formula 1, $X^1$ is N or $CR^1$, $X^2$ is N or $CR^2$, $X^3$ is N or $CR^3$, $X^4$ is N or $CR^4$, $X^5$ is N or $CR^5$, at least one of $X^1$ to $X^3$ is N, $R^1$ to $R^5$ are independently hydrogen, deuterium, a cyano group, a halogen, a substituted or unsubstituted C1 to C4 alkyl group, a substituted or unsubstituted C6 to C10 aryl group, a substituted or unsubstituted C3 to C40 silyl group, or a combination thereof, at least one of $R^1$ to $R^5$ is a cyano group, a halogen, a substituted or unsubstituted C1 to C4 alkyl group, a substituted or unsubstituted C6 to C10 aryl group, or a substituted or unsubstituted C3 to C40 silyl group, $X^6$ and $X^7$ are independently $CR^aR^b$ or $SiR^cR^d$, $R^a$ to $R^d$ are independently, hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, $X^8$ to $X^{10}$ are independently N or CH, at least one of $X^8$ to $X^{10}$ is N, M is Ir, Os, Pt, Pb, Re, Ru, or Pd, m and n are independently an integer of 1 or 2, and m+n is an integer of 3, wherein the substituted refers to a substitution where at least one hydrogen is replaced by deuterium, a halogen, a hydroxy group, an amino group, a C1 to C30 amine group, a nitro group, a C3 to C40 silyl group, a C1 to C30 alkyl group, C1 to 010 alkylsilyl group, C3 to C30 cycloalkyl group, a C6 to C30 aryl group, a C1 to C20 alkoxy group, or a cyano group.

In another embodiment of the present invention, a compound for an organic optoelectronic device is provided.

In yet another embodiment of the present invention, an organic optoelectronic device includes an anode and a cathode facing each other and one layered organic layer between the anode and the cathode, wherein the organic layer includes the compound according to one embodiment of the present invention.

In still another embodiment of the present invention, a display device including the organic optoelectronic device according to one embodiment of the present invention is provided.

Advantageous Effects

The organic optoelectronic device including the compound has excellent electrochemical and thermal stability and life-span characteristics, and high luminous efficiency at a low driving voltage.

DESCRIPTION OF REFERENCE NUMERALS INDICATING PRIMARY ELEMENTS IN THE DRAWINGS

Figure 1:
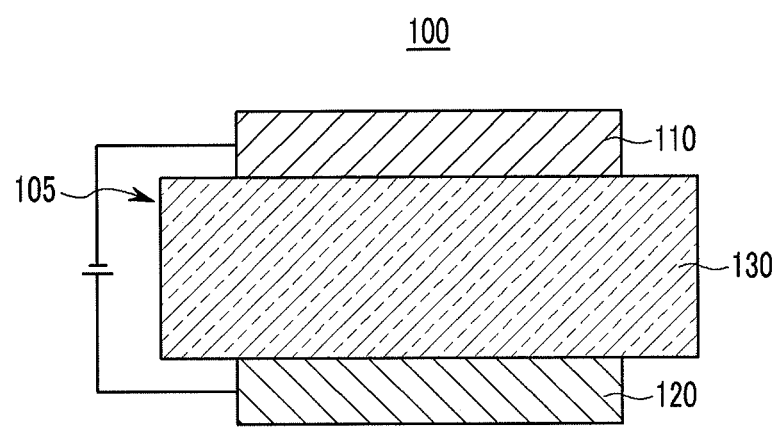
FIGS. 1 and 2 are cross-sectional views showing organic light emitting diodes according to various embodiments manufactured using the compound according to one embodiment of the present invention.

100: organic light emitting diode
105: organic layer
110: cathode
120: anode
130: emission layer
140: hole auxiliary layer
200: organic light emitting diode
230: emission layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C3 to C40 silyl group, a C1 to C30 alkyl group, a C1 to 010 alkylsilyl group, a C3 to C30 cycloalkyl group, a C6 to C30 aryl group, a C1 to C20 alkoxy group, a fluoro group, a C1 to 010 trifluoroalkyl group such as a trifluoromethyl group or a cyano group instead of at least one hydrogen of a substituent or a compound.

In addition, two adjacent substituents of the substituted halogen, halogen, hydroxy group, amino group, substituted or unsubstituted C1 to C20 amine group, nitro group, substituted or unsubstituted C3 to C40 silyl group, C1 to C30 alkyl group, C1 to 010 alkylsilyl group, C3 to C30 cycloalkyl group, C6 to C30 aryl group, C1 to C20 alkoxy group, fluoro group, C1 to 010 trifluoroalkyl group such as trifluoromethyl group and the like, or cyano group may be fused with each other to form a ring.

In the present specification, when specific definition is not otherwise provided, the term "hetero" refers to one including 1 to 3 hetero atoms selected from N, O, S, and P, and remaining carbons in a functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C20 alkyl group. More specifically, the alkyl group may be a C1 to 010 alkyl group or a C1 to C6 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a cyclic substituent where all elements have p-orbitals, and these p-orbitals forms conjugation, and includes a monocyclic or fused ring polycyclic (i.e., rings sharing adjacent pairs of carbon atoms) functional group.

More specifically, the substituted or unsubstituted aryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted fluorenyl group, or a combination thereof, but is not limited thereto.

In the present specification, "heteroaryl group" refers to aryl group including 1 to 3 hetero atoms selected from N, O, S, and P, and remaining carbons. When the heteroaryl group is a fused ring, each ring may include 1 to 3 hetero atoms.

More specifically, the substituted or unsubstituted heteroaryl group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, a substituted or unsubstituted dibenzothiophenyl group, or a combination thereof, but are not limited thereto.

In the present invention, the halogen refers to a fluoro group, a chloro group, a bromo group or an iodine group, for example a fluoro group.

In one embodiment of the present invention, a compound represented by Chemical Formula 1 is provided.

[Chemical Formula 1]

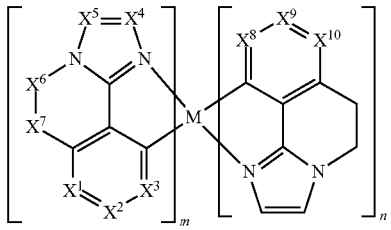

In Chemical Formula 1, $X^1$ is N or $CR^1$, $X^2$ is N or $CR^2$, $X^3$ is N or $CR^3$, $X^4$ is N or $CR^4$, $X^5$ is N or $CR^5$, at least one of $X^1$ to $X^3$ is N, $R^1$ to $R^5$ are independently hydrogen, deuterium, a cyano group, a halogen, a substituted or unsubstituted C1 to C4 alkyl group, a substituted or unsubstituted C6 to C10 aryl group, a substituted or unsubstituted C3 to C40 silyl group, or a combination thereof, at least one of $R^1$ to $R^5$ is a cyano group, a halogen, a substituted or unsubstituted C1 to C4 alkyl group, a substituted or unsubstituted C6 to C10 aryl group, or a substituted or unsubstituted C3 to C40 silyl group, $X^6$ and $X^7$ are independently $CR^aR^b$ or $SiR^cR^d$, $R^a$ to $R^d$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, $X^5$ to $X^{10}$ are independently N or CH, at least one of $X^5$ to $X^{10}$ is N, M is Ir, Os, Pt, Pb, Re, Ru, or Pd, m and n are independently an integer of 1 or 2, and m+n is an integer of 3, wherein the substituted refers to a substitution where at least one hydrogen is replaced by deuterium, a halogen, a hydroxy group, an amino group, a C1 to C30 amine group, a nitro group, a C3 to C40 silyl group, a C1 to C30 alkyl group, C1 to 010 alkylsilyl group, C3 to C30 cycloalkyl group, a C6 to C30 aryl group, a C1 to C20 alkoxy group, or a cyano group.

In the compound represented by Chemical Formula 1 of the present specification, a ligand represented as a bond number of m is hereinafter referred to be a "main ligand", and a ligand represented as a bond number of n is referred to be an "auxiliary ligand."

The main ligand includes a substituent other than hydrogen at one position of the $R^1$ to $R^5$ and thus may realize a compound having excellent thermal resistance stability and life-span characteristics and having high luminous efficiency at a low driving voltage.

Specifically, the compound according to one embodiment of the present invention may reduce a triplet-triplet extinction phenomenon, the most serious problem in an organic light emitting diode (OLED) by introducing one substituent selected from a cyano group, a substituted or unsubstituted C1 to C4 alkyl group, a substituted or unsubstituted C6 to C10 aryl group, or a substituted or unsubstituted C3 to C40 silyl group into at least one of the $R^1$ to $R^5$ and also, increase affinity to a host and thus suppress a triplet-triplet extinction phenomenon due to aggregation and resultantly, improve luminous efficiency and luminescence characteristics.

In addition, the present invention may provide a ligand having lower HOMO than a pyridine-phenyl ligand, that is, a wide bandgap and thus being appropriate for a blue dopant having a shorter wavelength by including N in at least one of the $X^1$ to $X^3$ of the main ligand and at least one of the $X^5$ to $X^{10}$ of the auxiliary ligand. In addition, the ligand has higher T1 than the pyridine-phenyl ligand and may be more appropriate for a phosphorescent blue dopant requiring high T1.

In one embodiment of the present invention, Chemical Formula 1 may be represented by Chemical Formulae 2 to 4 depending on a position of the N present in the $X^1$ to $X^3$ of the ligand.

[Chemical Formula 2]

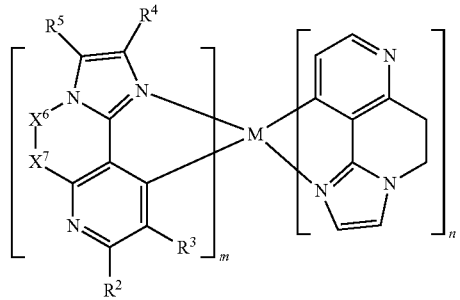

[Chemical Formula 3]

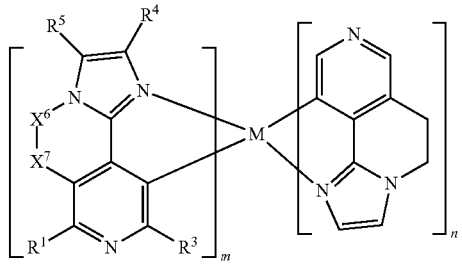

-continued

[Chemical Formula 4]

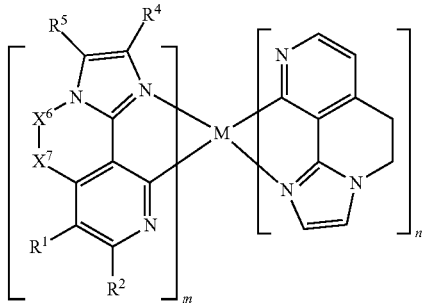

[Chemical Formula 6]

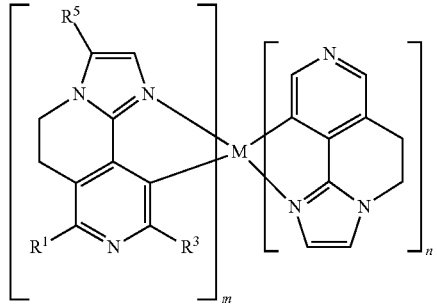

In Chemical Formulae 2 to 4, $R^1$ to $R^5$ are independently hydrogen, deuterium, a cyano group, a halogen, a substituted or unsubstituted C1 to C4 alkyl group, a substituted or unsubstituted C6 to C10 aryl group, a substituted or unsubstituted C3 to C40 silyl group, or a combination thereof, at least one of $R^1$ to $R^5$ is a cyano group, a halogen, a substituted or unsubstituted C1 to C4 alkyl group, a substituted or unsubstituted C6 to C10 aryl group, a substituted or unsubstituted C3 to C40 silyl group, or a combination thereof, $X^6$ and $X^7$ are independently $CR^aR^b$, or $SiR^cR^d$, $R^a$ to $R^d$ are independently, hydrogen, deuterium, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 silyl group, a halogen, a cyano group, a hydroxyl group, an amino group, a nitro group, a carboxyl group, or a combination thereof, M is Ir, Os, Pt, Pb, Re, Ru, or Pd, m and n are independently an integer of 1 or 2, and m+n is an integer of 3, wherein the substituted refers to a substitution where at least one hydrogen is replaced by deuterium, a halogen, a hydroxy group, an amino group, a C1 to C30 amine group, a nitro group, a C3 to C40 silyl group, a C1 to C30 alkyl group, C1 to 010 alkylsilyl group, C3 to C30 cycloalkyl group, a C6 to C30 aryl group, a C1 to C20 alkoxy group, or a cyano group.

For one example of the present invention, when the position of the substituent is fixed, the Chemical Formula 1 may be represented by one of Chemical Formulae 5 to 7.

[Chemical Formula 5]

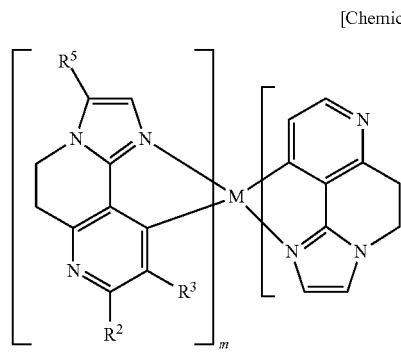

[Chemical Formula 7]

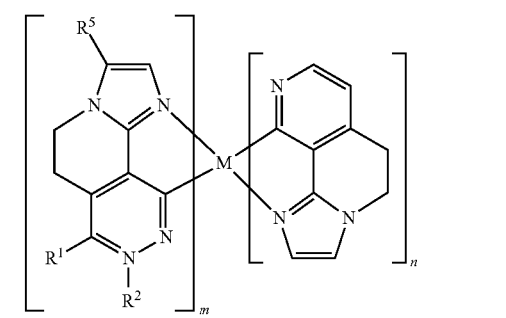

In Chemical Formulae 5 to 7, $R^1$ to $R^3$, $R^5$, M, m, and n are the same as defined in Chemical Formula 2 to Chemical Formula 4.

The compound of the present invention has a substituent at a pyridine ring or an imidazole ring and thus may remarkably improve a photo quantum yield (PQY) of a light emitting material for improving efficiency of a device compared with a complex including no substituent.

$R^1$ to $R^5$ are independently hydrogen, deuterium, a cyano group, a halogen, a substituted or unsubstituted C1 to C4 alkyl group, a substituted or unsubstituted C6 to C10 aryl group, a substituted or unsubstituted C3 to C40 silyl group, or a combination thereof, At least one of the $R^1$ to $R^5$ may be a cyano group, a methyl group, an ethyl group, an isopropyl group, a t-butyl group, a trimethylsilyl group, a fluorine group, a trifluoromethyl group, or a phenyl group.

Herein, the compound may not only reduce a triplet-triplet extinction phenomenon, the most serious problem in OLED but also increase affinity to a host and thus suppress a triplet-triplet extinction phenomenon due to aggregation and resultantly, improve luminous efficiency, luminescence characteristics, and a life-span compared with a pyridine-phenyl iridium compound.

In Chemical Formula 1, n and m may independently be an integer of 1 or 2, and n+m may be 3. Herein, at least one auxiliary ligand is included in Chemical Formula 1. Accordingly, the compound may be capable of color-tuning by including at least one auxiliary ligand.

Specific examples of the compound according to one embodiment of the present invention may be the compounds, but are not limited thereto.

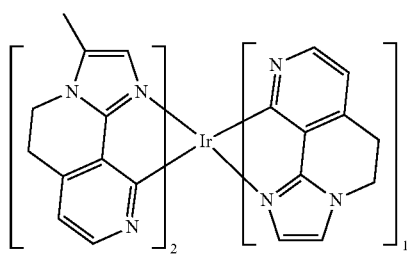
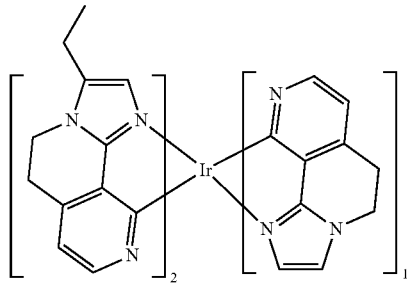
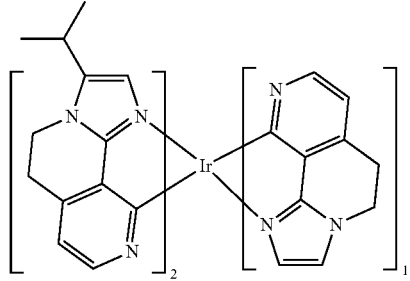
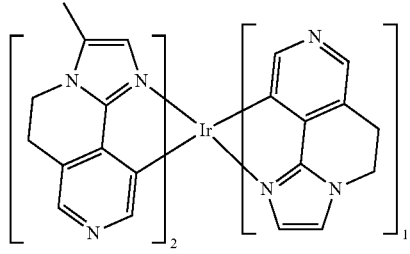
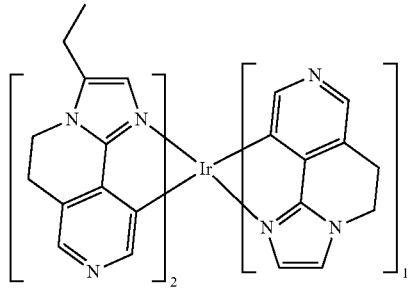
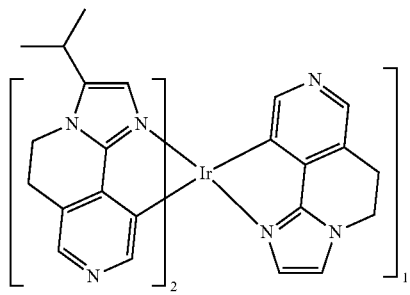
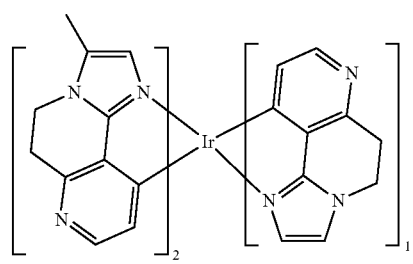
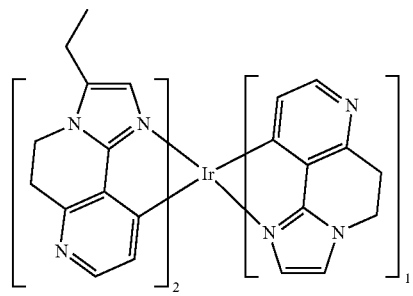
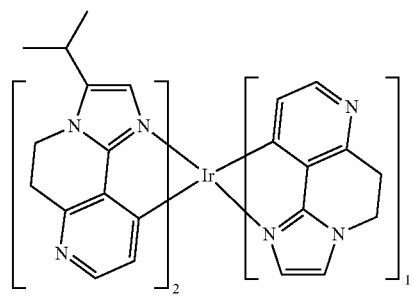
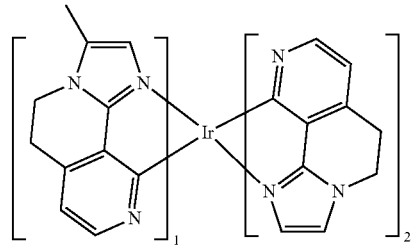
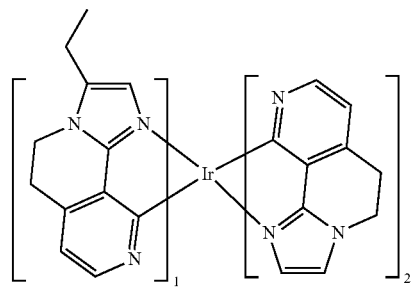
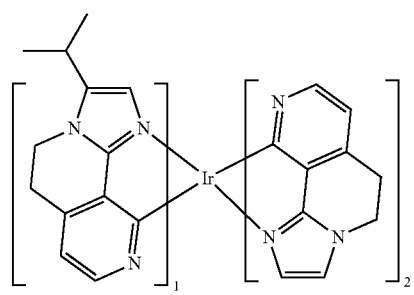

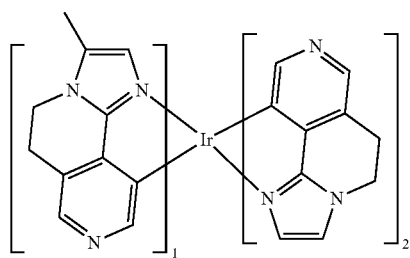
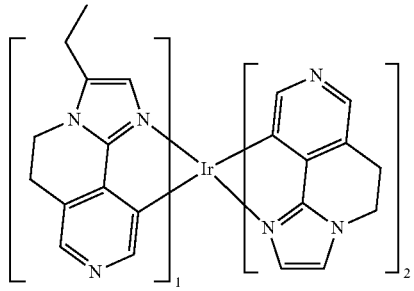
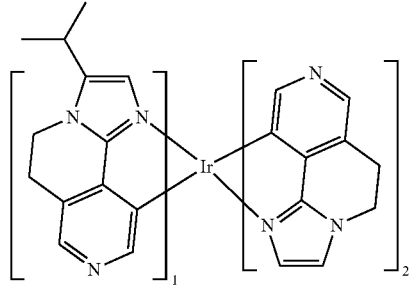
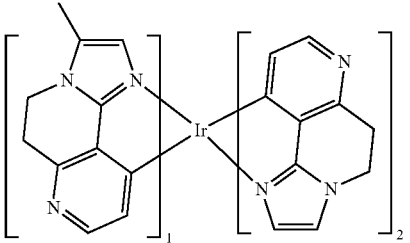
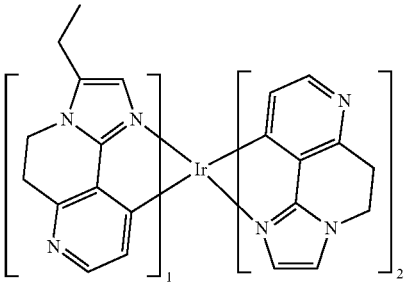
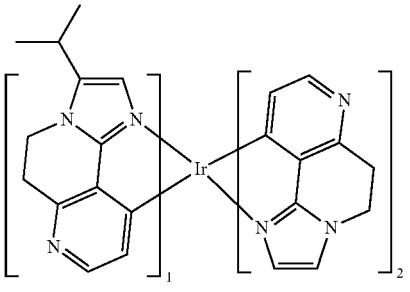
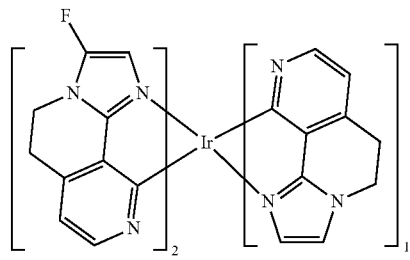
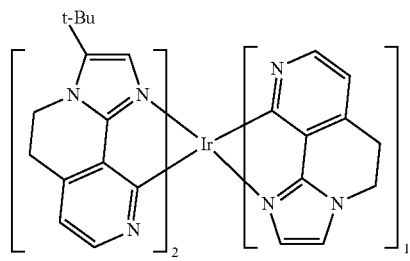
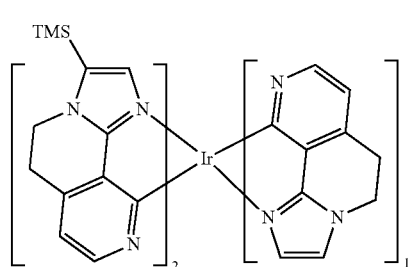
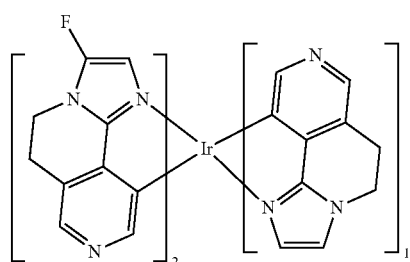
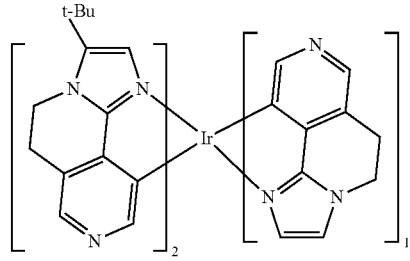
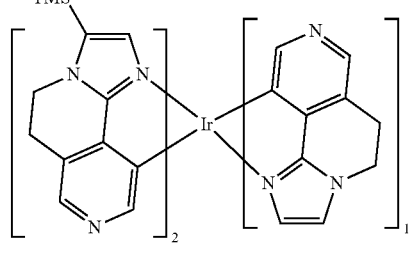

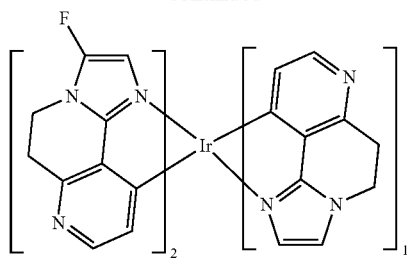
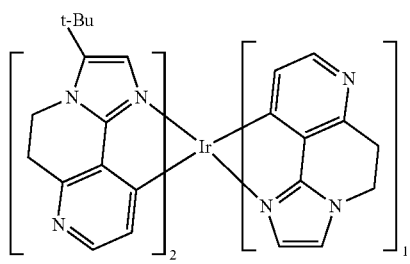
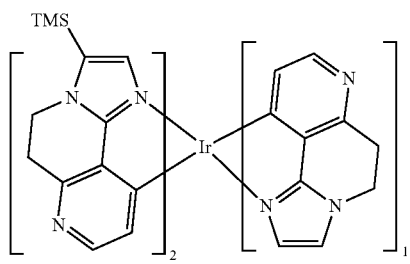
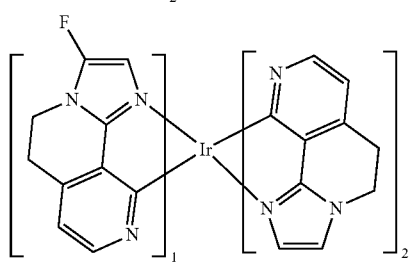
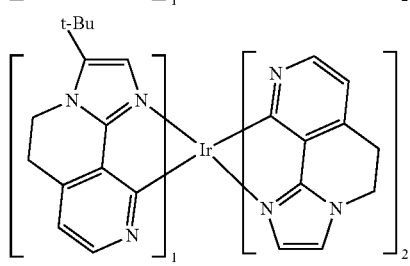
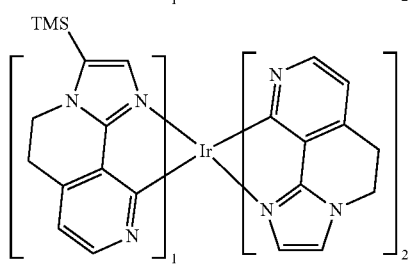
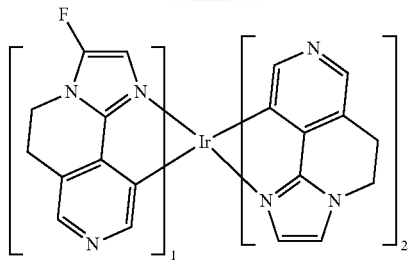
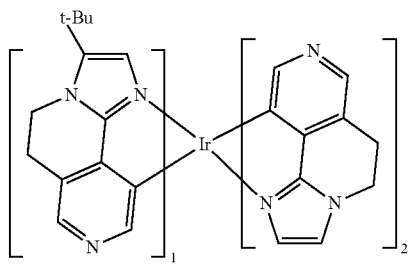
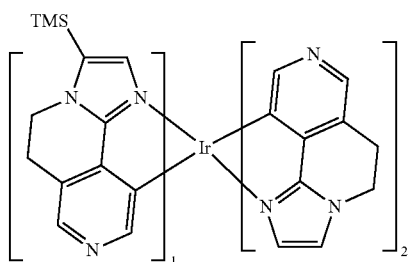
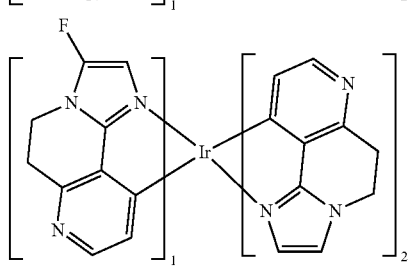
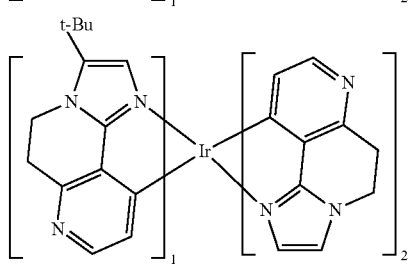
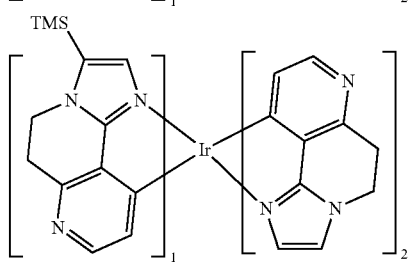

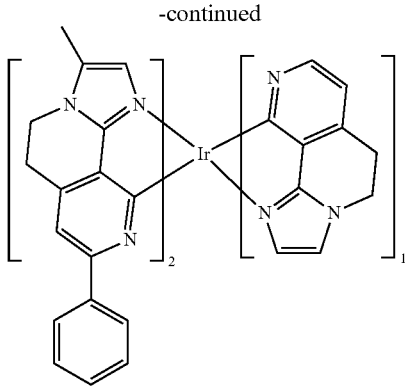
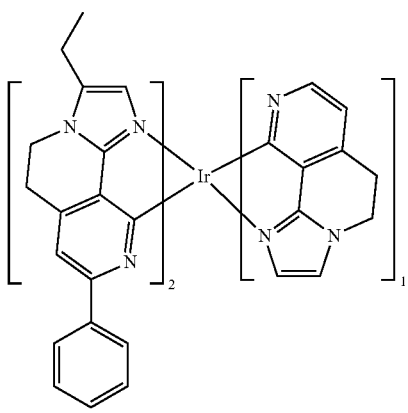
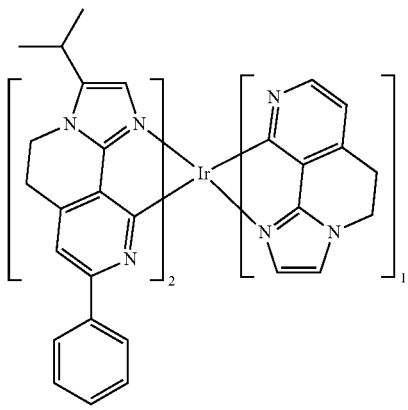
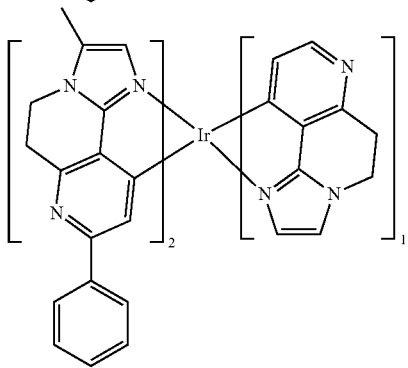
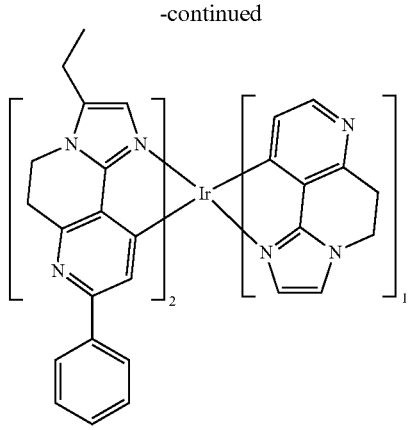
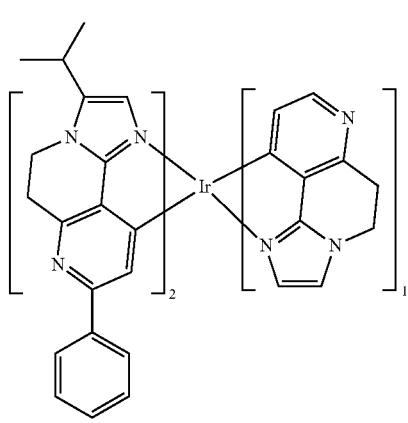
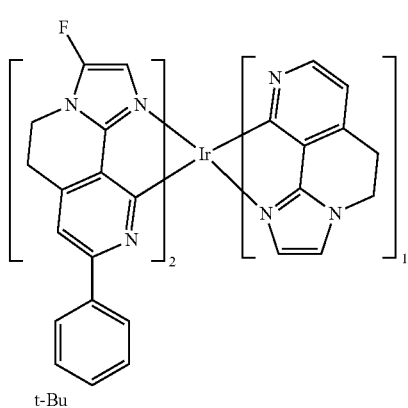
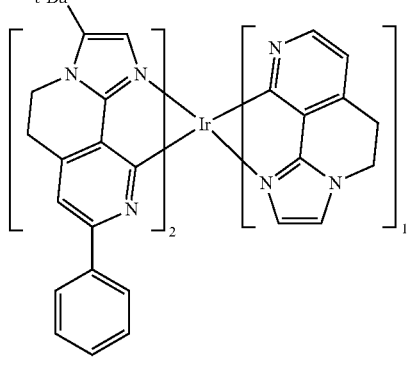

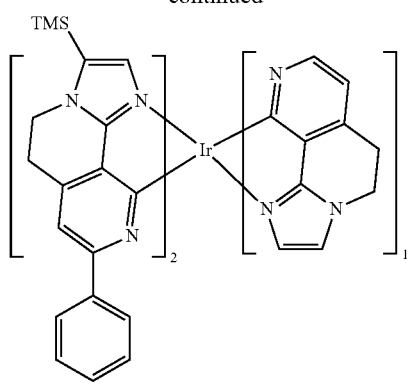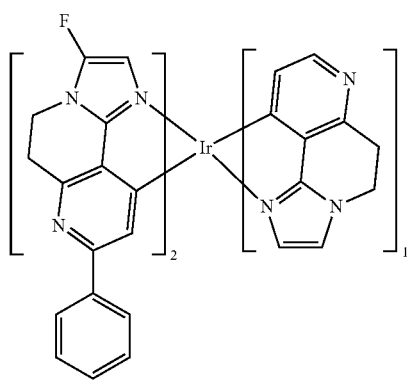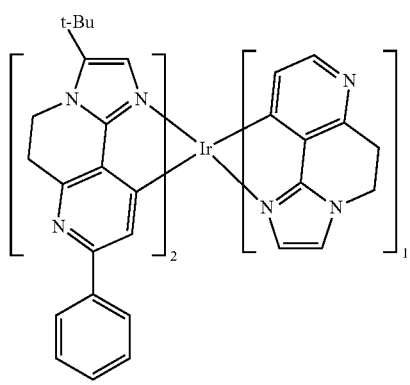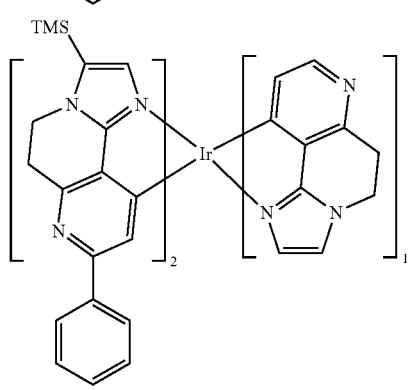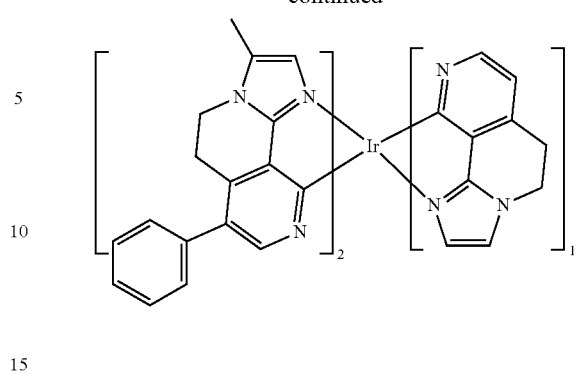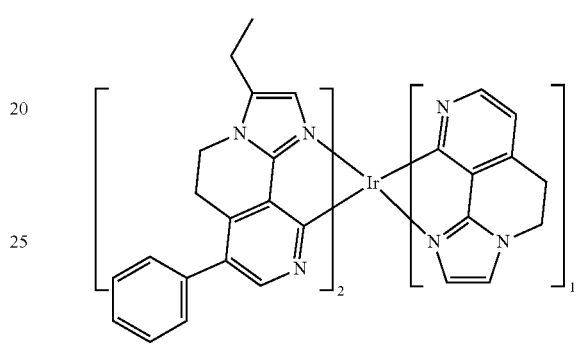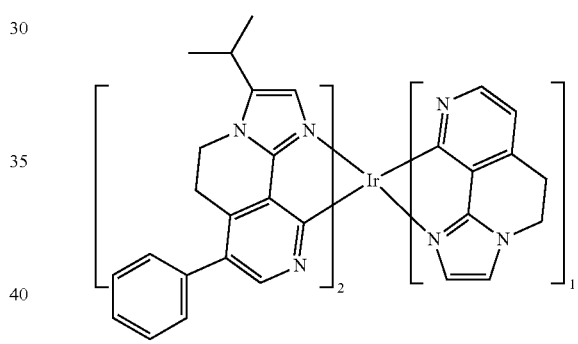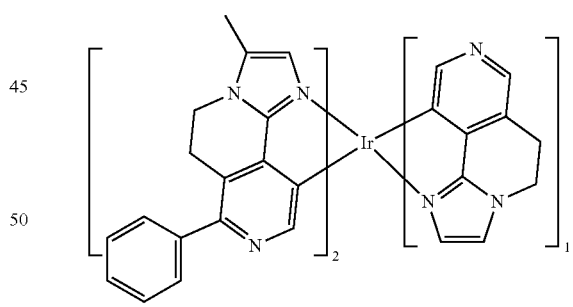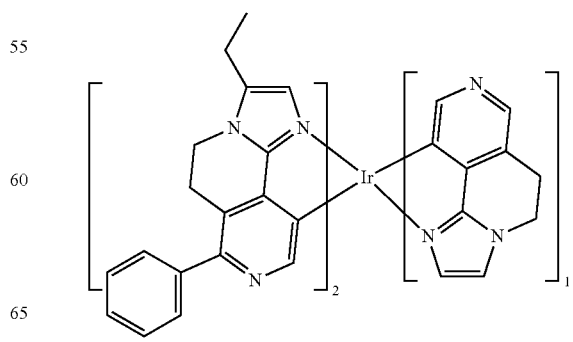

-continued
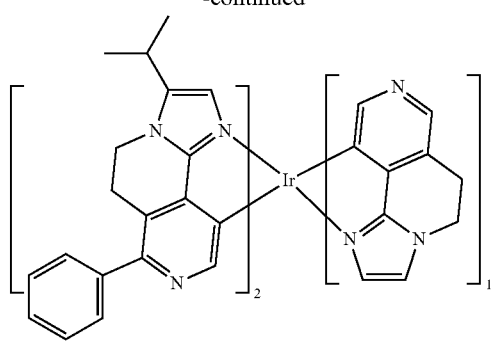
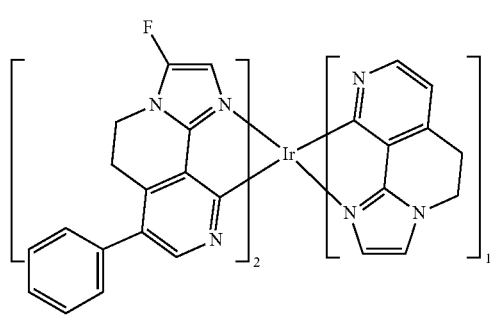
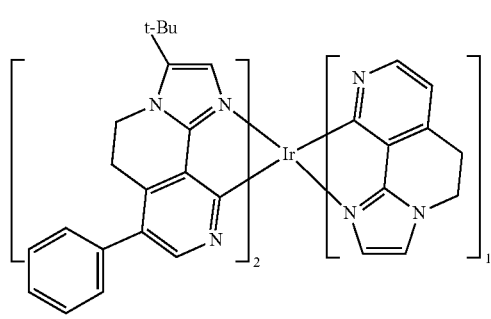
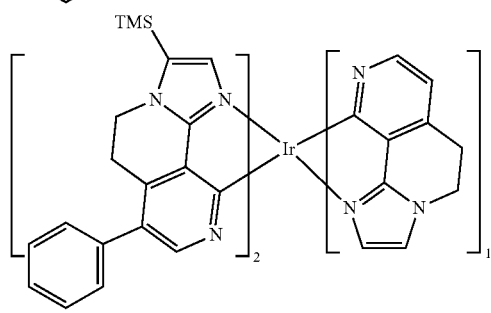
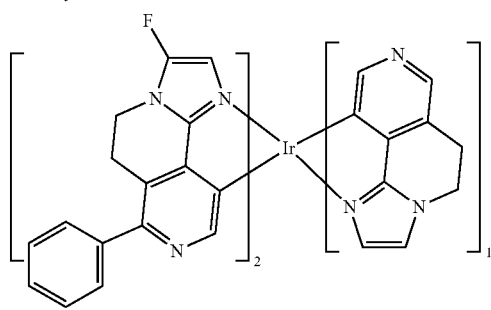
-continued
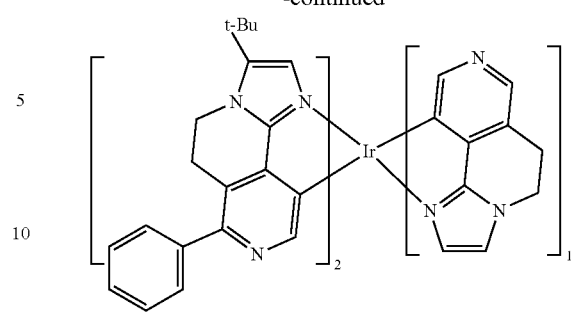
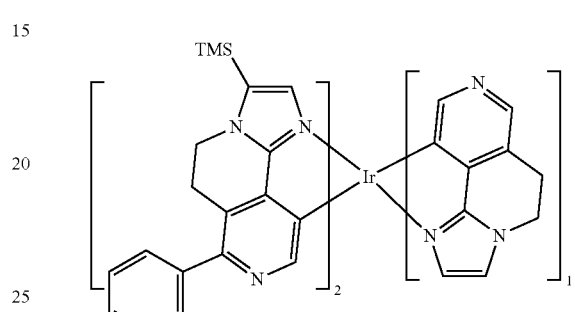
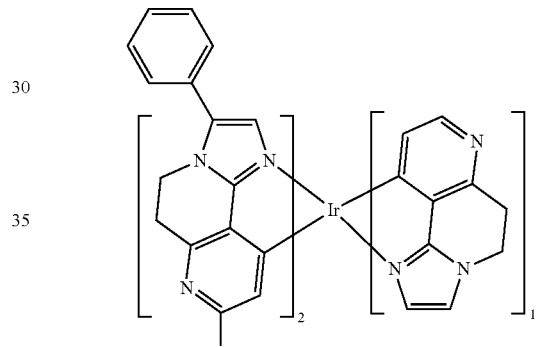
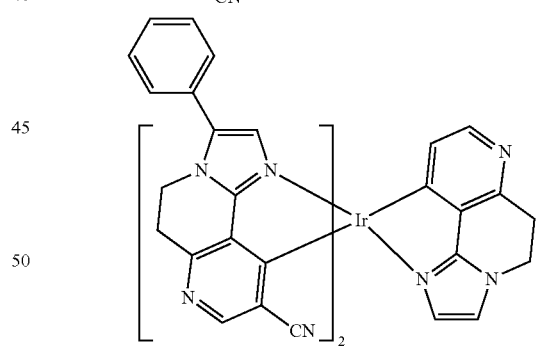
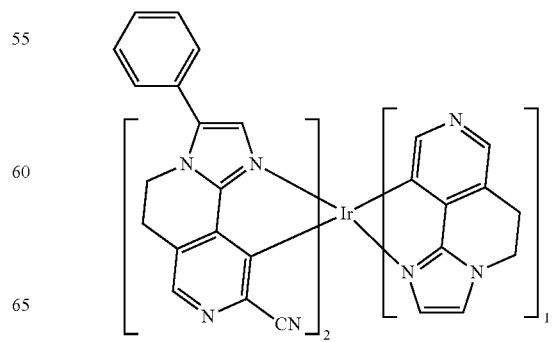

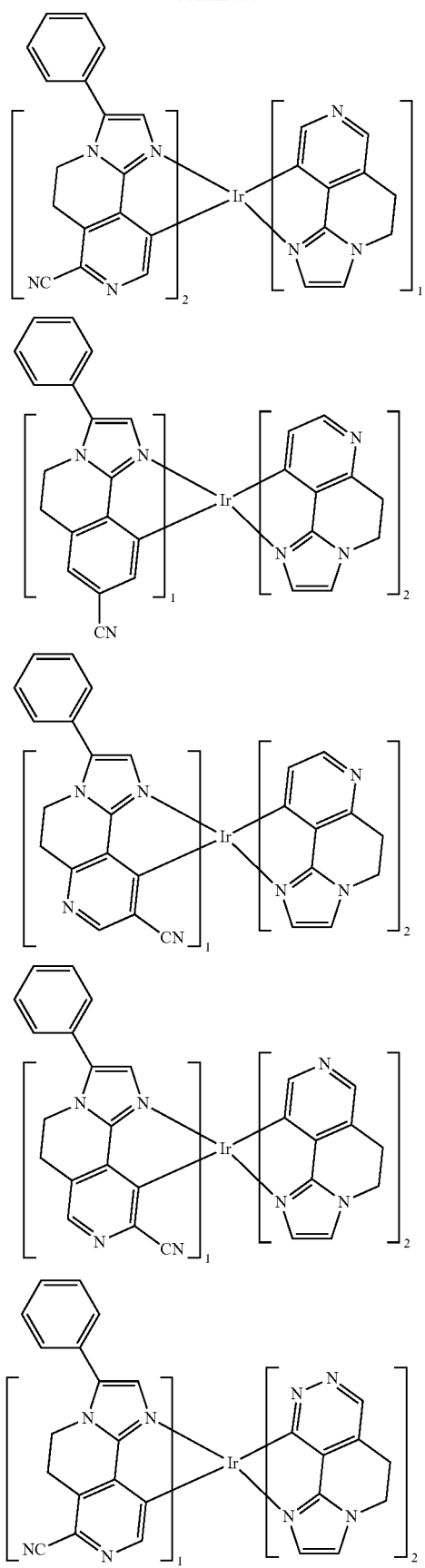
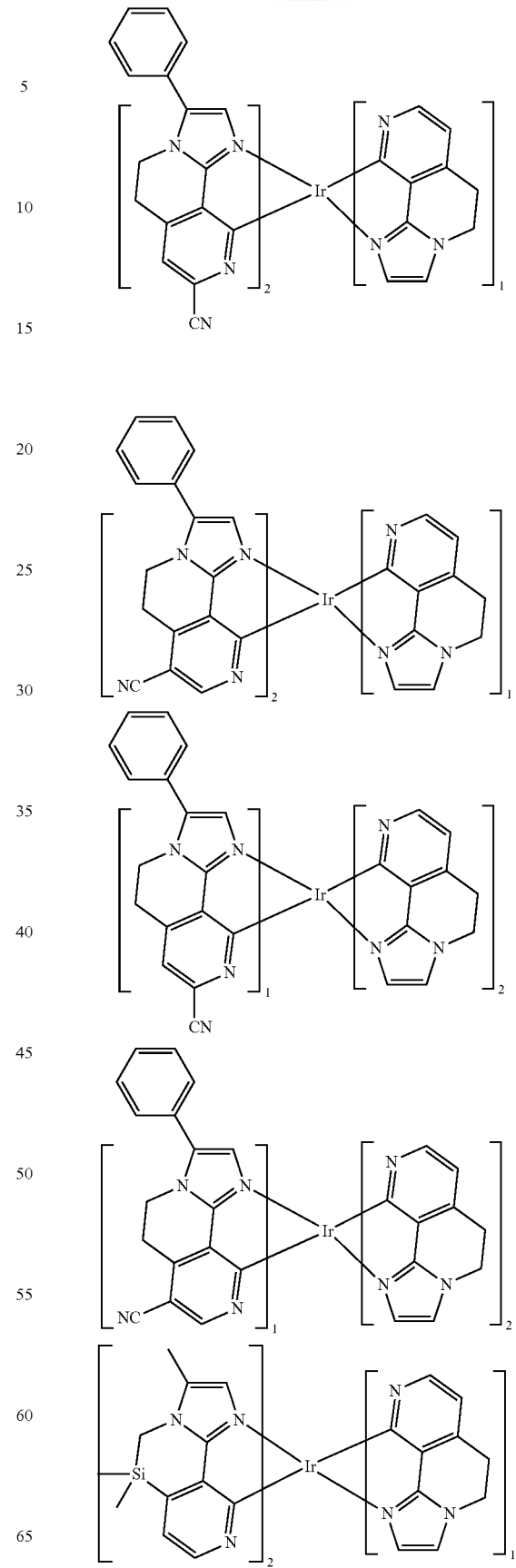

23
-continued
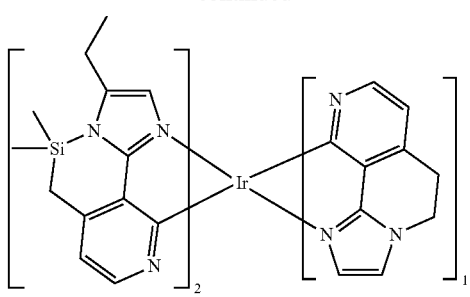
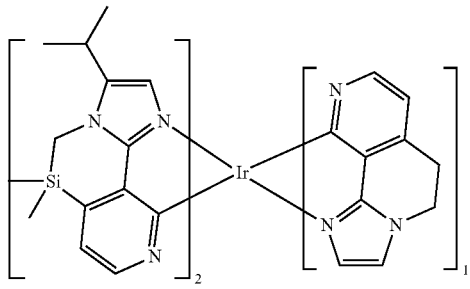
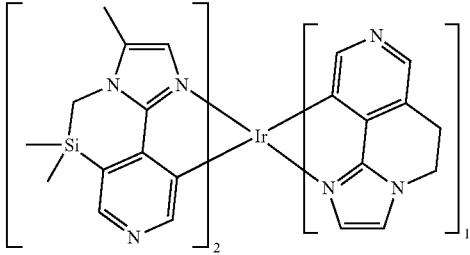
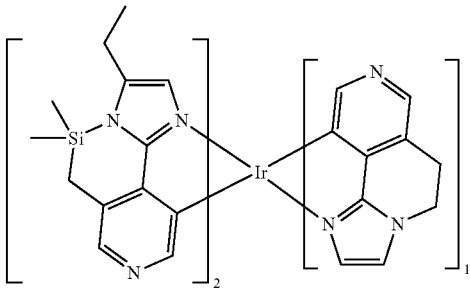
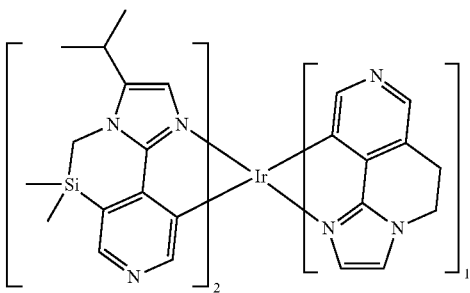
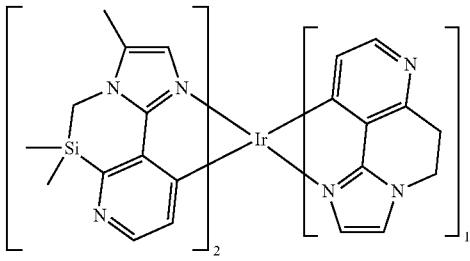
24
-continued
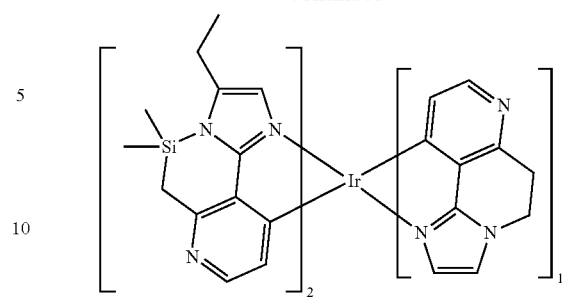
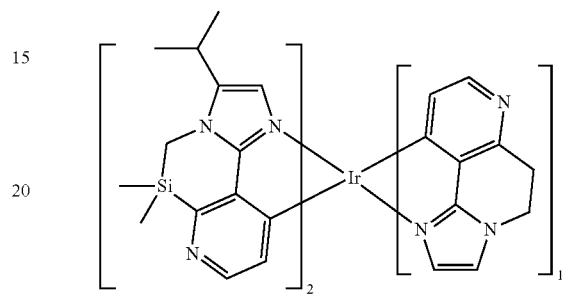
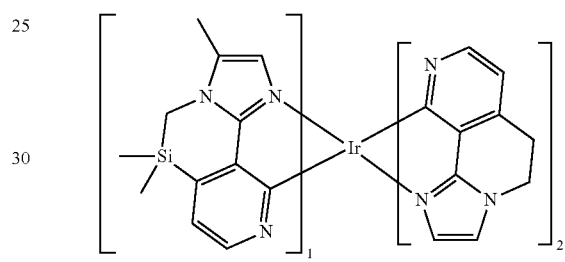
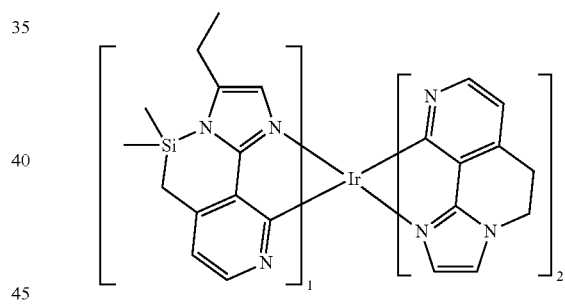
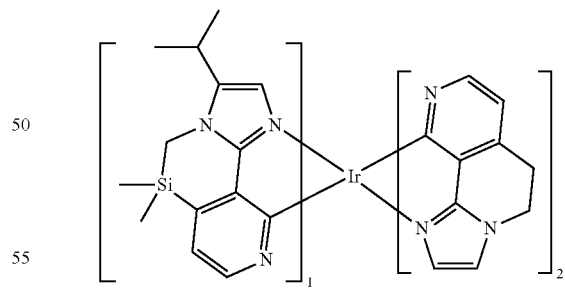
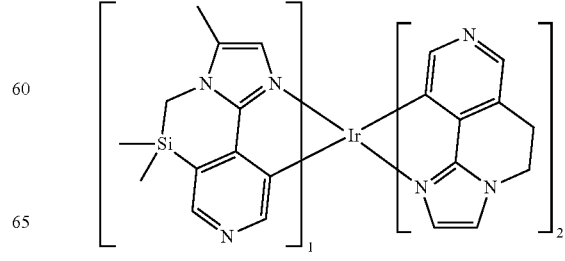

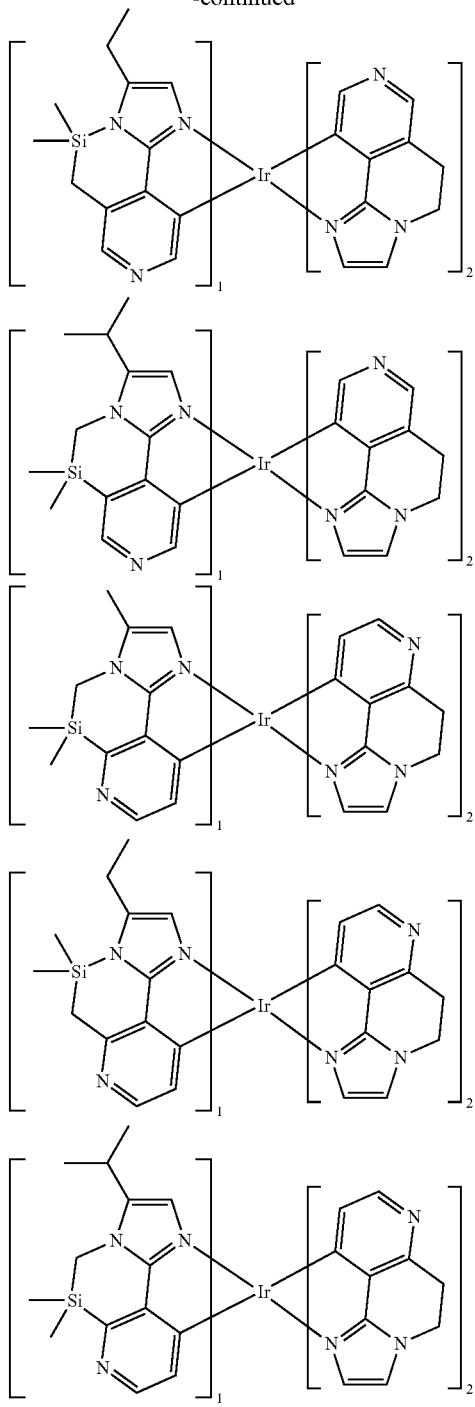

The compound may be used for an organic optoelectronic device.

Hereinafter, an organic optoelectronic device including the compound is described.

In another embodiment of the present invention, an organic optoelectronic device includes an anode and a cathode facing each other and one layered organic layer between the anode and the cathode, wherein the organic layer includes the compound.

The organic layer includes an emission layer, and the emission layer includes the compound.

Specifically, the compound may be included as a dopant of the emission layer.

The organic optoelectronic device including an organic layer including the compound has improved life-span characteristic, efficiency characteristics, electrochemical stability and thermal stability, and a lowered driving voltage.

More specifically, the organic optoelectronic device may be an organic light emitting diode.

Figure 2:
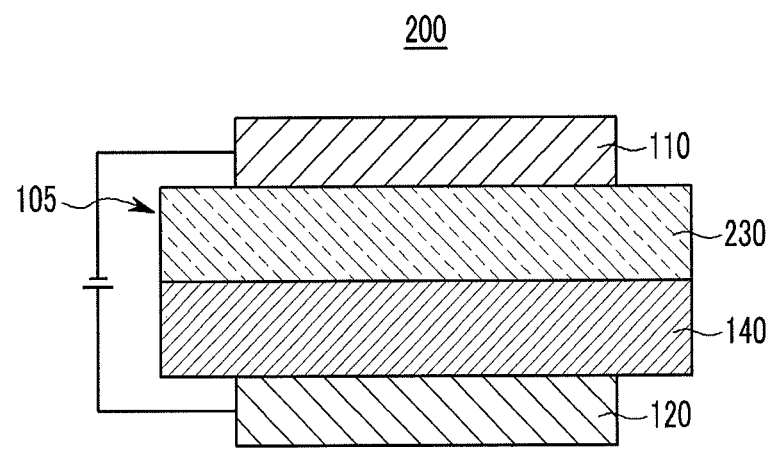

FIGS. 1 and 2 are cross-sectional views of an organic light emitting diode including the compound according to one embodiment of the present invention.

Referring to FIGS. 1 and 2, organic light emitting diodes 100 and 200 according to one embodiment of the present invention includes an anode 120, a cathode 110, and at least one organic layer 105 between the anode and the cathode.

The anode 120 includes an anode material, and the anode material is a material has a large work function to help hole injection into an organic layer. Specific examples of the anode material may be a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combination of a metal and an oxide such as ZnO:Al and SnO$_2$:Sb; or a conductive polymer such as poly(3-methylthiophene), poly[3,4-(ethylene-1,2-dioxy)thiophene] (PEDT), polypyrrole, and polyaniline, but are not limited thereto. It is preferable to include a transparent electrode including indium tin oxide (ITO) as an anode.

The cathode 110 includes a cathode material, and the cathode material has a small work function to help electron injection into an organic layer. Specific examples of the cathode material a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, LiF/Al, and BaF$_2$/Ca, but are not limited thereto. It is preferable to include a metal electrode including aluminum as a cathode.

First, referring to FIG. 1, the organic light emitting diode 100 includes an organic layer 105 including only an emission layer 130.

Referring to FIG. 2, a double-layered organic light emitting diode 200 includes an organic layer 105 including an emission layer 230 including an electron transport layer (ETL), and a hole transport layer (HTL) 140. As shown in FIG. 2, the organic layer 105 includes a double layer of the emission layer 230 and the hole transport layer (HTL) 140. The emission layer 130 also functions as an electron transport layer (ETL), and the hole transport layer (HTL) 140 layer has an improved binding property with a transparent electrode such as ITO or an improved hole transport capability. Even not shown in FIGS. 1 and 2, the organic layer 105 may further include an electron injection layer (EIL), an auxiliary electron transport layer (aETL), electron transport layer (ETL), a hole transport layer (HTL), an auxiliary hole transport layer (aHTL), a hole injection layer (HIL), and the like.

In FIGS. 1 and 2, the organic layer 105 selected from the emission layers 130 and 230, hole transport layer (HTL) 140, even not shown, an electron injection layer (EIL), an auxiliary electron transport layer (aETL), an electron transport layer (ETL), a hole transport layer (HTL), an auxiliary hole transport layer (aHTL), a hole injection layer (HIL), and a combination thereof may include the compound for an organic optoelectronic device.

Particularly, the compound for an organic optoelectronic device may be used in the emission layers 130 and 230, and may be used as a blue phosphorescent dopant material in the emission layer.

The organic light emitting diode may be fabricated by: forming an anode on a substrate; forming an organic layer in accordance with a dry coating method such as evaporation, sputtering, plasma plating, and ion plating, or a wet coating method such as spin coating, dipping, and flow coating; and providing a cathode thereon.

In yet another embodiment of the present invention, a display device including the organic optoelectronic device is provided.

Hereinafter, the embodiments are illustrated in more detail with reference to examples. These examples, however, are not in any sense to be interpreted as limiting the scope of the invention.

Preparation of Compound

Synthesis Example 1: Preparation of Dopant 1

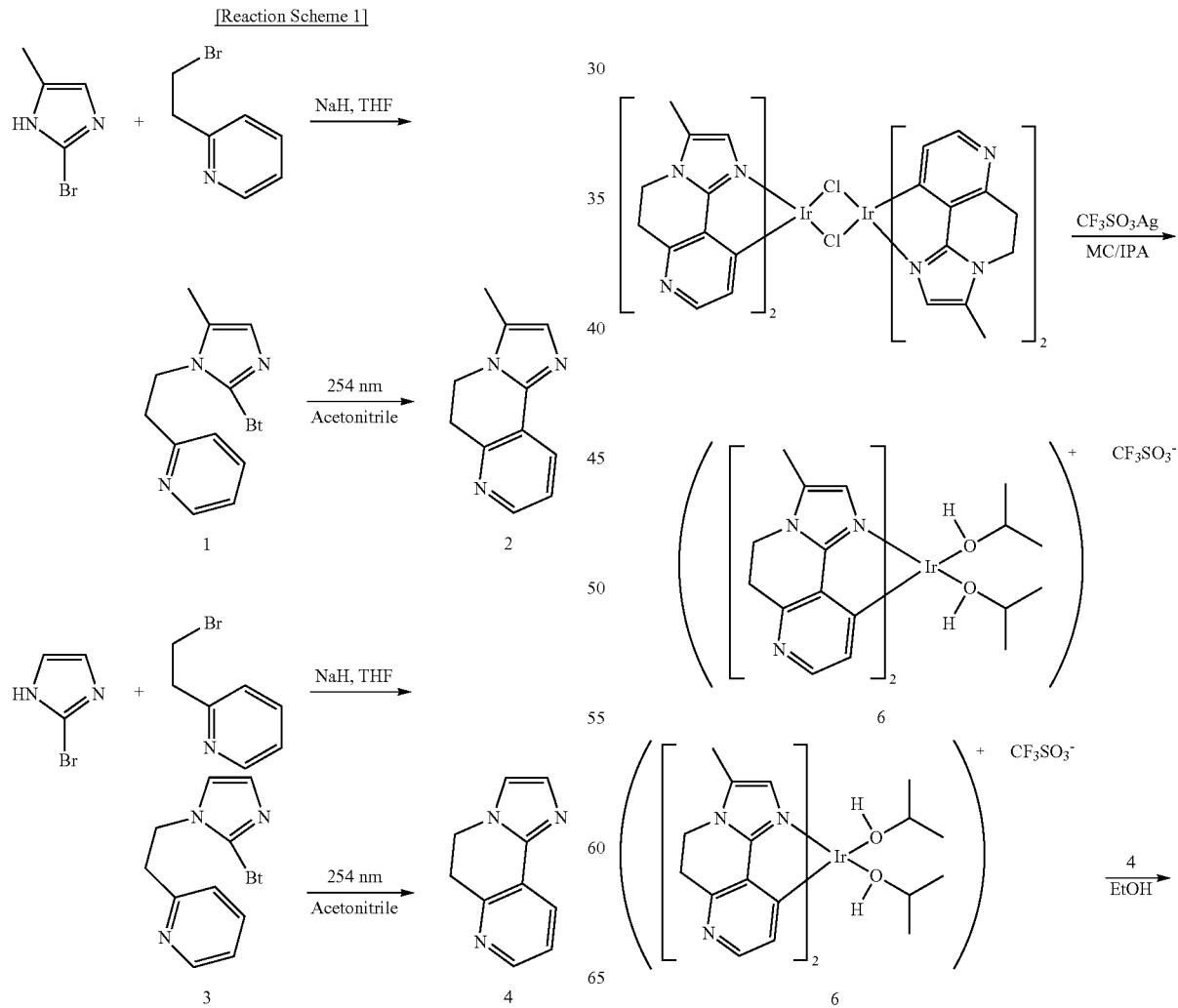

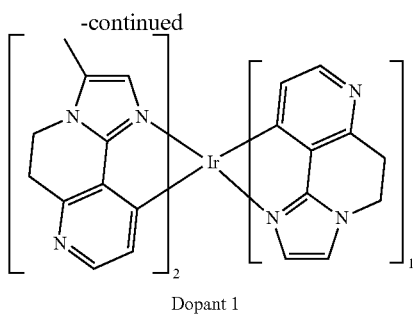

Dopant 1

Preparation of Intermediate Compound-1

20 g (0.124 mmol) of 2-bromo-5-methyl-1H-imidazole and 3.5 g (0.149 mmol) of sodium hydride were dissolved in 500 ml of THF (tetrahydrofuran) in a round-bottomed flask, and the solution was stirred and refluxed under a nitrogen stream for one hour. Subsequently, 36.9 g (0.198 mmol) of 2-(2-bromoethyl)pyridine was added thereto in a dropwise fashion, and the mixture was stirred and refluxed for 3 hours. When the reaction was complete, the remaining sodium hydride was quenched by using methanol. Subsequently, an organic layer was separated from an aqueous layer, and a solvent therein was all removed. The resultant was treated through column to chromatography (EA:Hexanes=1:1 (v/v)), obtaining 21 g of an intermediate compound-1 (a yield: 63.6%).

Preparation of Intermediate Compound-2

21 g (0.078 mmol) of the intermediate compound-1 was dissolved in nitrogen-purged acetonitrile, and the solution was put in a cylindrical quartz tube and radiated by energy of 254 nm for 5 hours. When a starting material disappears by examining the resultant through TLC, a solvent therein was removed. Subsequently, 30% sodium carbonate solution and methylene chloride were used to separate organic and aqueous layers. After separating the organic and aqueous layers, the solvent therein was all removed. The resultant was treated through column chromatography by using (EA: Hexane=1:1), obtaining 10 g of an intermediate compound-2 (a yield: 68%).

Preparation of Intermediate Compound-3

20 g (0.136 mmol) of 2-bromo-1H-imidazole and 3.9 g (0.163 mmol) of sodium hydride were dissolved in 500 ml of THF in a round-bottomed flask, and the solution was stirred and refluxed under a nitrogen stream for one hour. Subsequently, 40.5 g (0.217 mmol) of 2-(2-bromoethyl)pyridine was added thereto in a dropwise fashion, and the mixture was stirred and refluxed for 3 hours. When the reaction was complete, sodium hydride remaining there was quenched by using methanol. After separating an organic layer from an aqueous layer, a solvent therein was all removed. The resultant was treated through column chromatography, obtaining 26 g of an intermediate compound-3 (a yield: 76.4%).

Preparation of Intermediate Compound-4

26 g (0.1 mmol) of the intermediate compound-3 was dissolved in nitrogen-purged acetonitrile, and the solution was a cylindrical quartz tube and radiated by energy of 254 nm for 5 hours. When a starting material disappears by examining the resultant through TLC, a solvent therein was all removed. Subsequently, 30% sodium carbonate solution and methylene chloride were used to separate organic and aqueous layers. After the organic and aqueous layers, the solvent was all removed. The resultant was treated through column chromatography, obtaining 11 g of an intermediate compound-4 (a yield: 62.5%).

Preparation of Intermediate Compound-5

7.7 g (0.042 mmol) of the intermediate compound-2 and 5 g (0.017 mmol) of iridium chloride, 90 mL of 2-ethoxyethanol, and 30 mL of distilled water were put in a round-bottomed flask and then, heated and refluxed for 24 hours. When the reaction was complete, the resultant was cooled down to room temperature, and a solid produced during the reaction was filtered and washed with water and methanol. The solid was dried in a vacuum oven, obtaining 16 g of an intermediate compound-5 (a yield: 80%).

Preparation of Intermediate Compound-6

16 g (0.013 mmol) of the intermediate compound-5 was dissolved in MC (methylenechloride) in a round-bottomed flask. Then, 7.6 g (0.029 mmol) of silver trifluoro methanesulfonate was dissolved in isopropylalcohol, and the solution was added thereto in a dropwise fashion. The mixture was stirred at room temperature for one day, obtaining an intermediate compound-6, and the intermediate compound-6 was used in the following reaction without purification.

Preparation of Compound Dopant 1

10 g (0.012 mmol) of the intermediate compound-6 and 6.2 g (0.036 mmol) of the intermediate compound-4 were added to ethanol in a round-bottomed flask, and the mixture was refluxed under a nitrogen condition for one day. Subsequently, a solid produced therein was filtered and three times washed with ethanol and hexane. The solid was dissolved in dichloromethane and recrystallized with isopropyl alcohol, obtaining 5 g of a compound, Dopant 1 (a yield: 57%).

calcd. $C_{60}H_{51}IrN_6$: C, 52.59; H, 3.86; Ir, 26.30; N, 17.25. found: C, 52.52; H, 3.90; N, 17.21.

Synthesis Example 2: Preparation of Dopant 2

[Reaction Scheme 2]

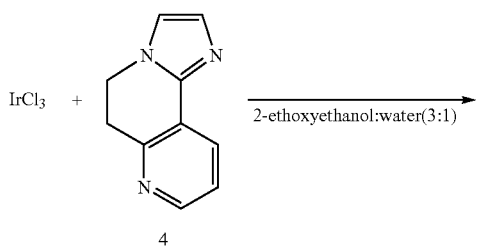

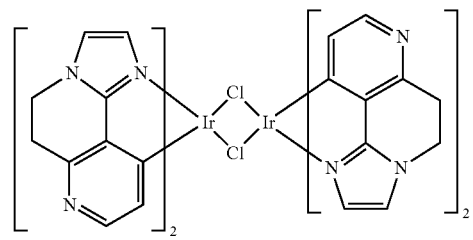

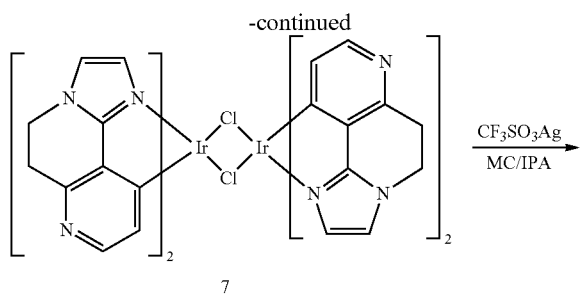

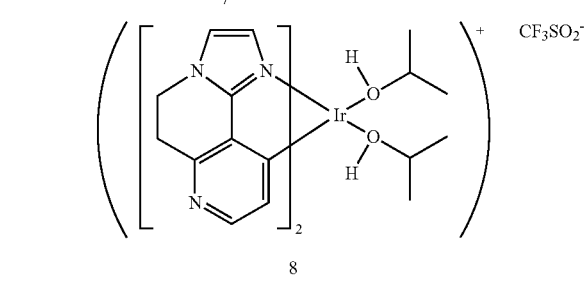

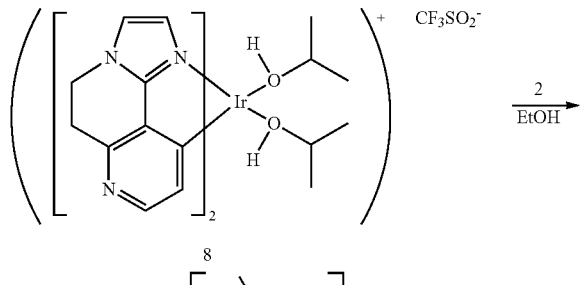

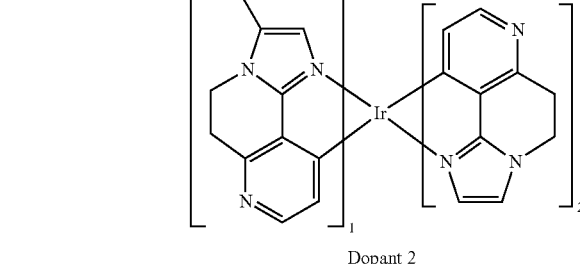

Dopant 2

Preparation of Intermediate Compound-7

7.2 g (0.042 mmol) of the intermediate compound-4, 5 g (0.017 mmol) of iridium chloride, 90 mL of 2-ethoxyethanol, and 30 mL of distilled water were put in a round-bottomed flask and then, heated and refluxed for 24 hours. When the reaction was complete, the resultant was cooled down to room temperature, and a solid produced during the reaction was filtered and washed with water and methanol. The solid was dried in a vacuum oven, obtaining 13 g of an intermediate compound-7 (a yield: 68%).

Preparation of Intermediate Compound-8

13 g (0.011 mmol) of the intermediate compound-7 was dissolved in MC in a round-bottomed flask. Then, a solution obtained by dissolving 6.5 g (0.025 mmol) of silver trifluoro methanesulfonate in isopropylalcohol was added thereto in a dropwise fashion. The mixture was stirred at room temperature for one day, obtaining an intermediate compound-8, and the intermediate compound-8 was used in the following reaction without purification.

Preparation of Compound Dopant 2

8 g (0.010 mmol) of the intermediate compound-8, the intermediate compound-2 5.5 g (0.030 mmol), and ethanol were put in a round-bottomed flask and refluxed under a nitrogen condition for one day. The solid was filtered and three times washed with ethanol and hexane. The solid was dissolved in dichloromethane and crystallized again with isopropyl alcohol, obtaining 4 g of a compound, Dopant 2 (a yield: 56%).

calcd. $C_{60}H_{51}IrN_6$: C, 51.94; H, 3.66; Ir, 26.82; N, 17.59. found: C, 51.92; H, 3.70; N, 17.56.

Synthesis Example 3: Preparation of Dopant 3

[Reaction Scheme 3]

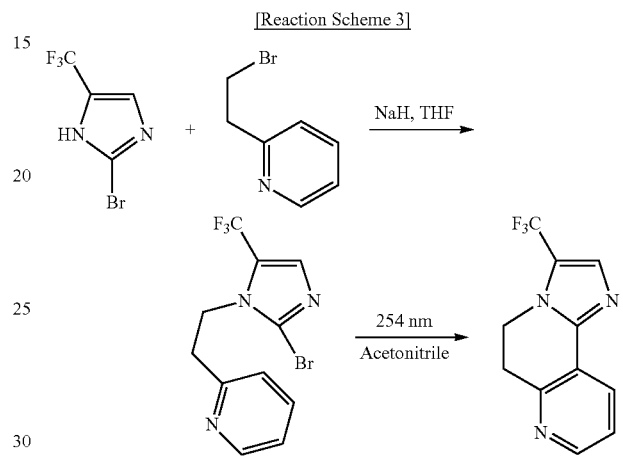

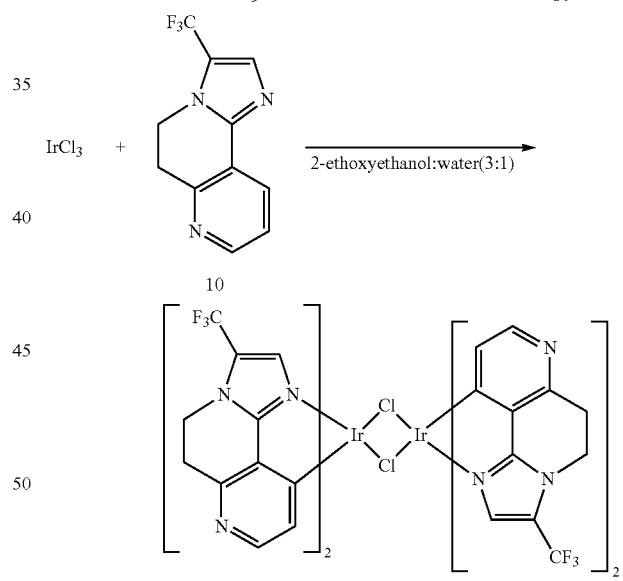

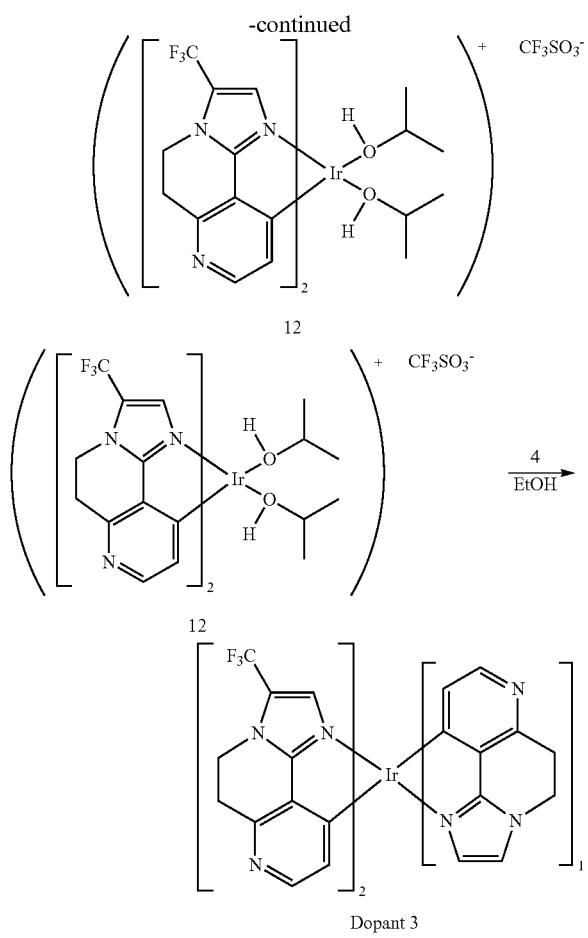

Dopant 3

Preparation of Intermediate Compound-9

15 g (0.070 mmol) of 2-bromo-5-trifluoromethyl-1H-imidazole and 2 g (0.083 mmol) of sodium hydride were dissolved in 400 ml of THF in a round-bottomed flask, and the solution was stirred and refluxed under a nitrogen stream for 1 hour. Subsequently, 20.8 g (0.111 mmol) of 2-(2-bromoethyl)pyridine was added thereto in a dropwise fashion, and the mixture was stirred and refluxed for 3 hours. When the reaction was complete, sodium hydride remaining therein was quenched with methanol. After separating an organic layer from an aqueous layer, a solvent therein was all removed. The resultant was treated through column chromatography, obtaining 15 g of an intermediate compound-9 (a yield: 68%).

Preparation of Intermediate Compound-10

15 g (0.045 mmol) of the intermediate compound-9 was dissolved in nitrogen-purged acetonitrile, and the solution was put in a cylindrical quartz tube and radiated by energy of 254 nm for 5 hours. When a starting material disappears by examining the resultant through TLC, a solvent therein was removed. Subsequently, 30% sodium carbonate solution and methylene chloride were used to separate an organic layer and an aqueous layer. After separating the organic layer and the aqueous layer, the solvent was all removed. The resultant was treated through column chromatography, obtaining 6 g of an intermediate compound-10 (a yield: 53%).

Preparation of Intermediate Compound-11

6 g (0.025 mmol) of the intermediate compound-10, 3 g (0.010 mmol) of iridium chloride, 60 mL of 2-ethoxyethanol, and 20 mL of distilled water were put in a round-bottomed flask and heated and refluxed for 24 hours. When the reaction was complete, the resultant was cooled down to room temperature, and a solid produced during the reaction was filtered and washed with water and methanol. The solid was dried in a vacuum oven, obtaining 10 g of an intermediate compound-11 (a yield: 70%).

Preparation of Intermediate Compound-12

10 g (0.007 mmol) of the intermediate compound-11 was dissolved in MC in a round-bottomed flask. Then, a solution obtained by dissolving 4.6 g (0.018 mmol) of silver trifluoro methanesulfonate in isopropylalcohol was added thereto in a dropwise fashion. The mixture was stirred at room temperature for one day, obtaining an intermediate compound-12, and the intermediate compound-12 was used in the following reaction without purification.

Preparation of Compound Dopant 3

5 g (0.005 mmol) of the intermediate compound-12, 2.8 g (0.016 mmol) of the intermediate compound-4, and ethanol were put in a round-bottomed flask and then, refluxed under a nitrogen condition for one day. Then, a solid produced therein was filtered and three times washed with ethanol and hexane. The solid was dissolved in dichloromethane and crystallized again with isopropyl alcohol, obtaining 3 g of a compound, Dopant 3 (a yield: 66%).

calcd. $C_{60}H_{51}IrN_6$: C, 45.82; H, 2.64; F, 13.59; Ir, 22.92; N, 15.03. found: C, 45.92; H, 2.70; N, 14.56.

Synthesis Example 4: Preparation of Dopant 4

[Reaction Scheme 4]

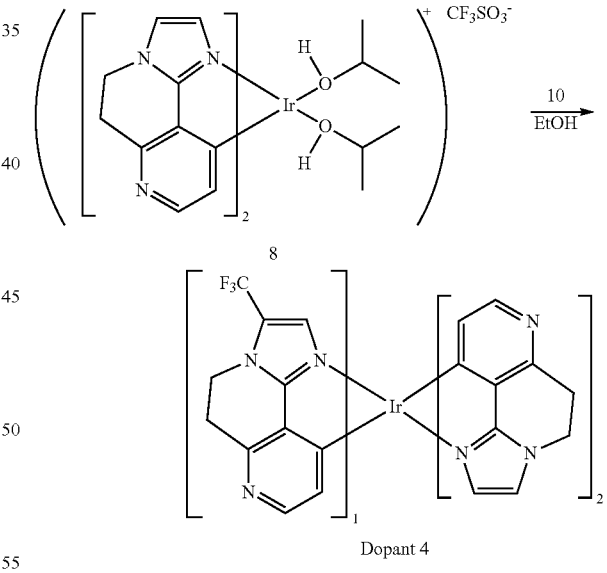

Dopant 4

Preparation of Compound Dopant 4

5 g (0.006 mmol) of the intermediate compound-8, 4.5 g (0.018 mmol) of the intermediate compound-10, and ethanol were put in a round-bottomed flask and refluxed under a nitrogen condition for one day. Then, a solid produced therein was filtered and three times washed with ethanol and hexane. The solid was dissolved in dichloromethane and crystallized again with isopropyl alcohol, obtaining 3.2 g of a compound Dopant 4 (a yield: 67%).

calcd. $C_{60}H_{51}IrN_6$: C, 48.31; H, 3.01; F, 7.39; Ir, 24.94; N, 16.35. found: C, 48.22; H, 3.09; N, 16.26.

Synthesis Example 5: Preparation of Dopant 5

[Reaction Scheme 5]

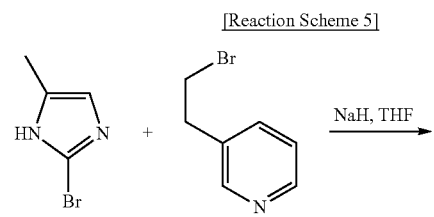
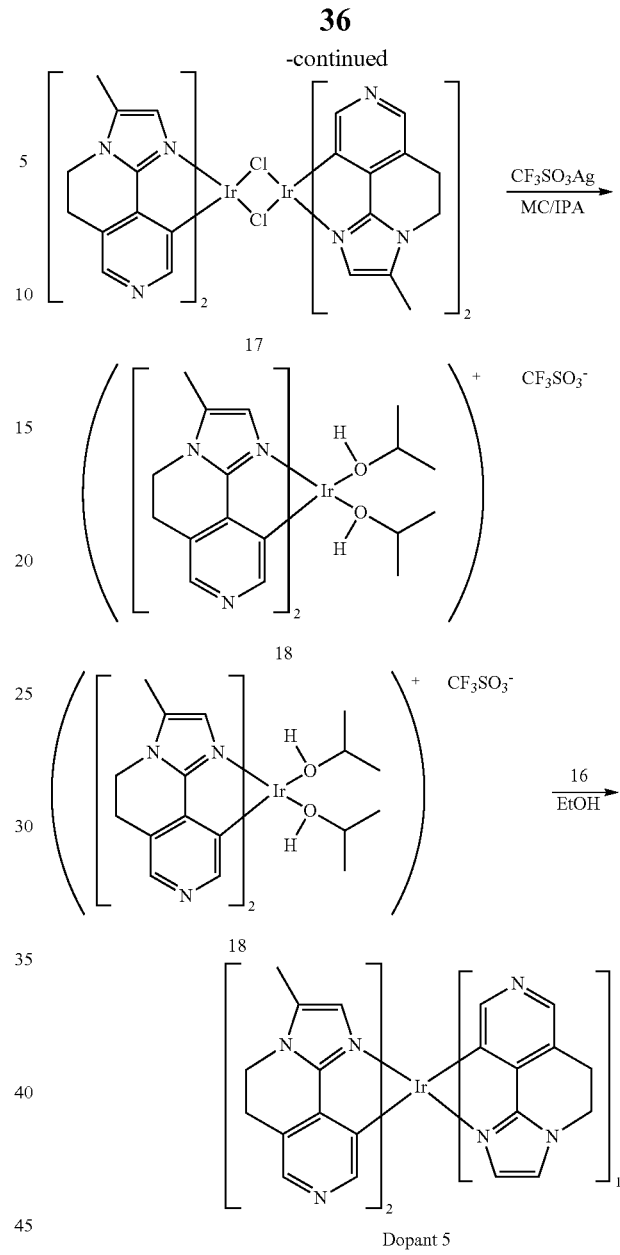
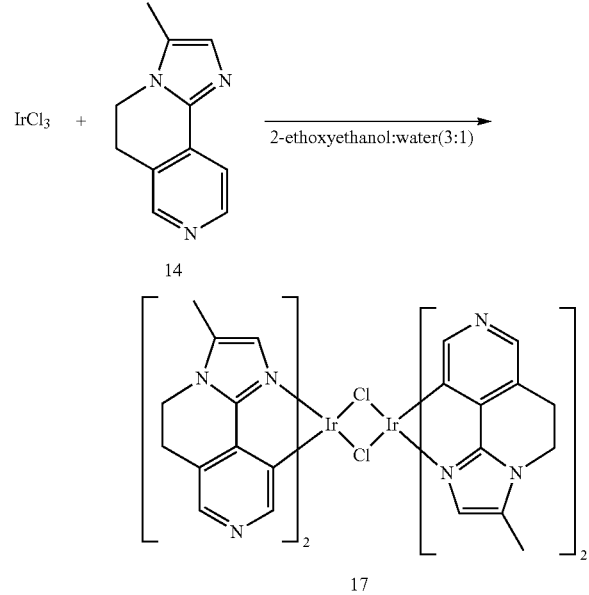

Preparation of Intermediate Compound-13

20 g (0.124 mmol) of 2-bromo-5-methyl-1H-imidazole and 3.5 g (0.149 mmol) of sodium hydride were dissolved in 500 ml of THF in a round-bottomed flask, and the solution was stirred and refluxed under a nitrogen stream for one hour. Subsequently, 36.9 g (0.198 mmol) of 3-(2-bromoethyl)pyridine was added thereto in a dropwise fashion, and the mixture was stirred and refluxed for 3 hours. When the reaction was complete, sodium hydride remaining therein was quenched with methanol. After separating an organic layer and an aqueous layer, a solvent therein was all removed. The resultant was treated through column chromatography, obtaining 19 g of an intermediate compound-13 (a yield: 57.5%).

Preparation of Intermediate Compound-14

19 g (0.091 mmol) of the intermediate compound-13 was dissolved in nitrogen-purged acetonitrile, and the solution was put in a cylindrical quartz tube and radiated by energy of 254 nm for 5 hours. When a starting material disappears by examining the resultant through TLC, a solvent was removed. Then, 30% sodium carbonate solution and methylene chloride were used to separate an organic layer and an aqueous layer. After separating the organic layer and the aqueous layer, a solvent therein was all removed. A resultant therefrom was treated through column chromatography, obtaining 8 g of an intermediate compound-14 (a yield: 60%).

Preparation of Intermediate Compound-15

20 g (0.136 mmol) of 2-bromo-1H-imidazole and 3.9 g (0.163 mmol) of sodium hydride were dissolved in 500 ml of THF in a round-bottomed flask, and the solution was stirred and refluxed under a nitrogen stream for one hour. Then, 40.5 g (0.217 mmol) of 3-(2-bromoethyl)pyridine was added thereto in a dropwise fashion, and the mixture was stirred and refluxed for 3 hours. When the reaction was complete, sodium hydride remaining therein was quenched by methanol. After separating an organic layer and an aqueous layer, a solvent therein was all removed. Subsequently, a resultant therefrom was treated through column chromatography, obtaining 23 g of an intermediate compound-15 (a yield: 67%).

Preparation of Intermediate Compound-16

23 g (0.091 mmol) of the intermediate compound-15 was dissolved in nitrogen-purged acetonitrile, and the solution was put in a cylindrical quartz tube and radiated by energy of 254 nm for 5 hours. When a starting material disappears by examining the resultant through TLC, a solvent therein was removed. Then, 30% sodium carbonate solution and methylene chloride were used to separate an organic layer and an aqueous layer. After separating the organic layer and the aqueous layer, the solvent therein was all removed. A resultant therefrom was treated through column chromatography, obtaining 11 g of an intermediate compound-16 (a yield: 70%).

Preparation of Intermediate Compound-17

7.7 g (0.042 mmol) of the intermediate compound-14, 5 g (0.017 mmol) of iridium chloride, 90 mL of 2-ethoxyethanol, and 30 mL of distilled water were put in a round-bottomed flask and then, heated and refluxed for 24 hours. When the reaction was complete, the resultant was cooled down to room temperature, and a solid produced during the reaction was filtered and washed with water and methanol. The solid was dried in a vacuum oven, obtaining 12 g of an intermediate compound-17 (a yield: 60%).

Preparation of Intermediate Compound-18

12 g (0.010 mmol) of the intermediate compound-17 was dissolved in MC in a round-bottomed flask. Subsequently, a solution obtained by dissolving 5.7 g (0.022 mmol) of silver trifluoro methanesulfonate in isopropylalcohol was added thereto in a dropwise fashion. The mixture was stirred at room temperature for one day, obtaining an intermediate compound-18, and the intermediate compound-18 was used in the following reaction without purification.

Preparation of Compound Dopant 5

6 g (0.007 mmol) of the intermediate compound-18, 3.7 g (0.022 mmol) of the intermediate compound-16, and ethanol were put in a round-bottomed flask and refluxed under a nitrogen condition for one day. Then, a solid produced therein was filtered and three times washed with ethanol and hexane. The solid was dissolved in dichloromethane, and the solution was recrystallized with isopropyl alcohol, obtaining 3.5 g of a compound, Dopant 5 (a yield: 66%).

calcd. $C_{60}H_{51}IrN_6$: C, 52.59; H, 3.86; Ir, 26.30; N, 17.25. found: C, 52.57; H, 3.89; N, 17.29.

Synthesis Example 6: Preparation of Dopant 6

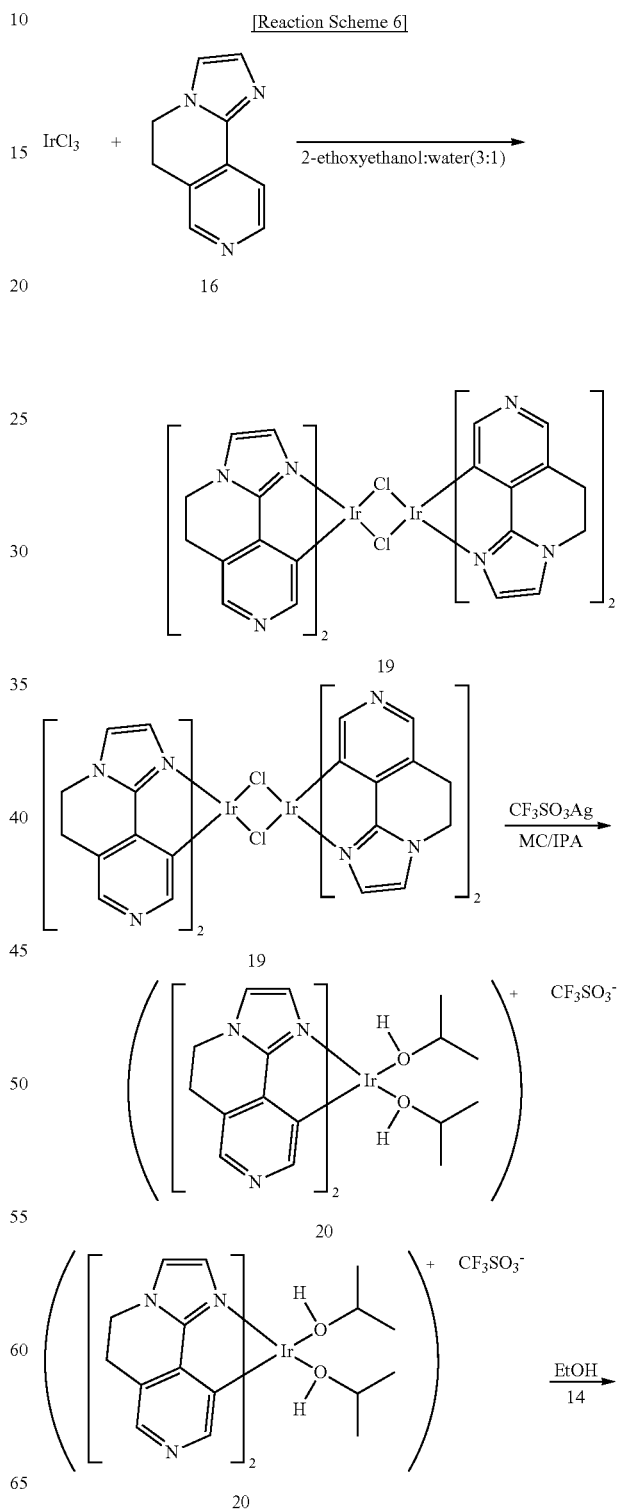

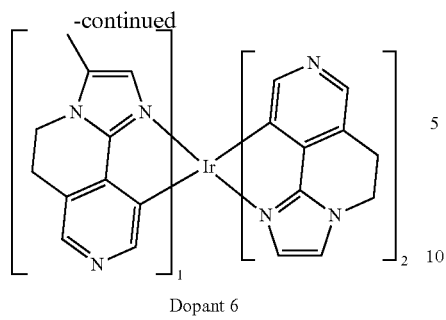

Dopant 6

Preparation of Intermediate Compound-19

7.2 g (0.042 mmol) of the intermediate compound-16, 5 g (0.017 mmol) of iridium chloride, 90 mL of 2-ethoxyethanol, and 30 mL of distilled water were heated and refluxed in a round-bottomed flask for 24 hours. When the reaction was complete, the resultant was cooled down to room temperature, and a solid produced during the reaction was filtered and washed with water and methanol. The solid was dried in a vacuum oven, obtaining 12 g of an intermediate compound-19 (a yield: 62%).

Preparation of Intermediate Compound-20

12 g (0.010 mmol) of the intermediate compound-19 was dissolved in MC in a round-bottomed flask. Subsequently, a solution obtained by dissolving 6 g (0.023 mmol) of silver trifluoro methanesulfonate in isopropylalcohol was added thereto in a dropwise fashion. The mixture was stirred at room temperature for one day, obtaining an intermediate compound-20, and the intermediate compound-20 was used for the following reaction without purification.

Preparation of Compound Dopant 6

6 g (0.007 mmol) of the intermediate compound-20, 4.2 g (0.022 mmol) of the intermediate compound-14, and ethanol were put in a round-bottomed flask and refluxed under a nitrogen condition for one day. Then, a solid produced therein was filtered and three times washed with ethanol and hexane. The solid was dissolved in dichloromethane and crystallized again with isopropyl alcohol, obtaining 3 g of a compound, Dopant 6 (a yield: 56%).

calcd. $C_{60}H_{51}IrN_6$: C, 51.94; H, 3.66; Ir, 26.82; N, 17.59. found: C, 51.98; H, 3.60; N, 17.58.

(Manufacture of Organic Light Emitting Diode)

Comparative Example 1

A glass substrate coated with ITO (Indium tin oxide) as a 1500 Å-thick thin film was ultrasonic wave-washed with distilled water. Subsequently, the glass substrate was ultrasonic wave-washed with a solvent such as isopropyl alcohol, acetone, methanol, and the like and dried, then, moved to a plasma washer and cleaned for 5 minutes, and then, moved to a vacuum evaporator. This obtained ITO transparent electrode was used as an anode, and HTM (a-NPD(4,4'-bis [N-(1-napthyl)-N-phenyl-amino]biphenyl) represented by Chemical Formula Z-1 was vacuum-deposited on the ITO substrate upper to form a hole transport layer (HTL).

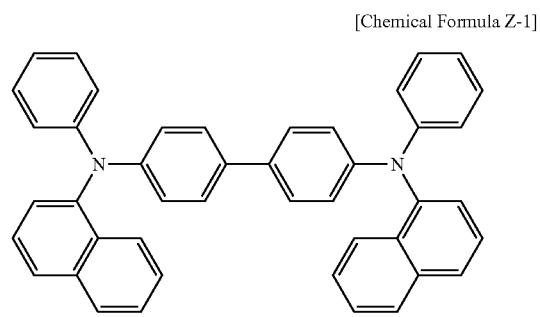

[Chemical Formula Z-1]

[Chemical Formula Z-2]

On the hole transport layer (HTL), CDBP represented by Chemical Formula Z-2 as a host doped with Fir6 (iridium (III) bis(4,6-difluorophenylpyridinato)tetrakis(1-pyrazolyl) borate) represented by Chemical Formula Z-3 as a blue phosphorescent dopant in an amount of 10 wt % was vacuum-deposited to form a 300 Å-thick emission layer.

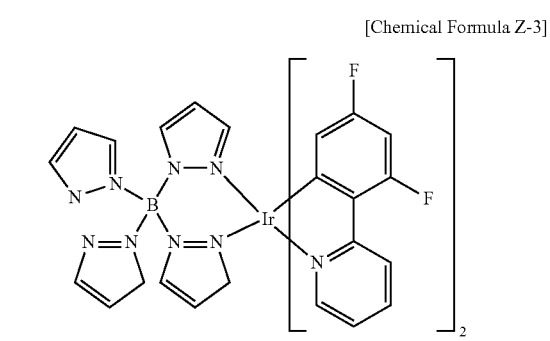

[Chemical Formula Z-3]

Then, on the emission layer, 50 Å-thick BAlq (bis(2-methyl-8-quinolinolato-N1,O8)-(1,1'-Biphenyl-4-olato)aluminum)) represented by Chemical Formula Z-4 and 250 Å-thick Alq3 (tris(8-hydroxyquinolinato)aluminium) represented by Chemical Formula Z-5 were sequentially accumulated, forming an electron transport layer (ETL). On the electron transport layer (ETL), 5 Å-thick LiF and 1000 Å-thick Al were sequentially vacuum-deposited to form a cathode, manufacturing an organic light emitting diode.

[Chemical Formula Z-4]

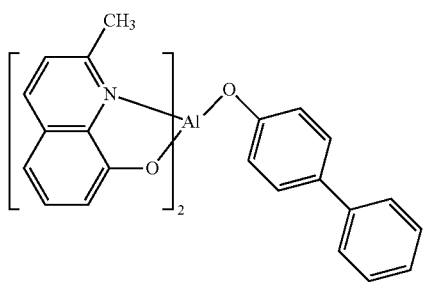

[Chemical Formula Z-5]

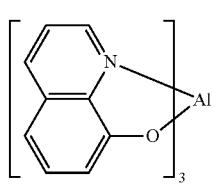

Comparative Example 2

An organic light emitting diode was manufactured according to the same method as Comparative Example 1 except for using a compound represented by Chemical Formula T-1 in an amount of 10 wt % instead of the Fir6 represented by Chemical Formula Z-3 as the blue phosphorescent dopant.

[T-1]

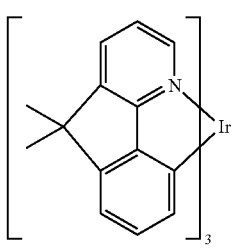

Device Example 1

An organic light emitting diode was manufactured according to the same method as Comparative Example 1 except for using the dopant 1 according to Synthesis Example 1 in an amount of 10 wt % instead of the Fir6 represented by Chemical Formula Z-3 as the blue phosphorescent dopant.

Device Example 2

An organic light emitting diode was manufactured according to the same method as Device Example 1 except for using the dopant 2 according to Synthesis Example 2 in an amount of 10 wt % instead of the dopant 1 according to Synthesis Example 1 as the blue phosphorescent dopant.

Device Example 3

An organic light emitting diode was manufactured according to the same method as Device Example 1 except for using the dopant 3 according to Synthesis Example 3 in an amount of 10 wt % instead of the dopant 1 according to Synthesis Example 1 as the blue phosphorescent dopant.

Device Example 4

An organic light emitting diode was manufactured according to the same method as Device Example 1 except for using the dopant 4 according to Synthesis Example 4 in an amount of 10 wt % instead of the dopant 1 according to Synthesis Example 1 as the blue phosphorescent dopant.

Device Example 5

An organic light emitting diode was manufactured according to the same method as Device Example 1 except for using the dopant 5 according to Synthesis Example 5 in an amount of 10 wt % instead of the dopant 1 according to Synthesis Example 1 as the blue phosphorescent dopant.

Device Example 6

An organic light emitting diode was manufactured according to the same method as Device Example 1 except for using the dopant 6 according to Synthesis Example 6 in an amount of 10 wt % instead of the dopant 1 according to Synthesis Example 1 as the blue phosphorescent dopant.

(Performance Measurement of Organic Light Emitting Diode)

Current density change and luminance change depending on a voltage of each organic light emitting diode according to Device Examples 1 to 6 and Comparative Examples 1 and 2 were measured and luminous efficiency was evaluated, and life-span characteristics were also evaluated. Specific measurement methods were as follows, and the results were shown in the following Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The luminance, current density, and voltage obtained from the (1) and (2) were used to calculate current efficiency (cd/A) at the same luminance (9000 cd/m$^2$).

(4) Life-Span Evaluation

A life-span was evaluated by measuring time taken until luminous efficiency was reduced down to 3%, and relative life-spans of the compounds provided in the present invention are provided based on 100% of Comparative Example.

TABLE 1

| | Chemical Formula | Luminous efficiency (cd/A) | Device life-span (h) T50 (%) at 10 mA/cm² |
|---|---|---|---|
| Comparative Example 1 | Z-3 | 5.1 | 10 |
| Comparative Example 2 | T-1 | 6.1 | 55 |
| Device Example 1 | D-1 | 9.8 | 125 |
| Device Example 2 | D-2 | 10.7 | 110 |
| Device Example 3 | D-3 | 11.7 | 85 |
| Device Example 4 | D-4 | 10.5 | 87 |
| Device Example 5 | D-5 | 8.1 | 105 |
| Device Example 6 | D-6 | 8.7 | 99 |

As shown in Table 1, each device manufactured by using the compounds provided in the present invention exhibits much excellent luminous efficiency and life-span. Accordingly, the compounds of the present invention may be used as a material for manufacturing a satisfactory organic light emitting diode.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound represented by Chemical Formula 1:

[Chemical Formula 1]

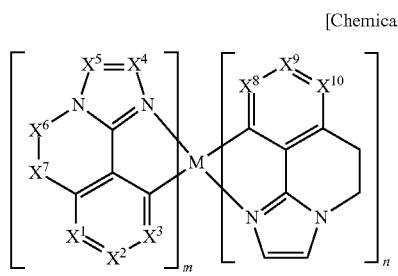

wherein, in Chemical Formula 1, $X^1$ is N or $CR^1$, $X^2$ is N or $CR^2$, $X^3$ is N or $CR^3$, $X^4$ is N or $CR^4$, $X^5$ is N or $CR^5$, at least one of $X^1$ to $X^3$ is N, $R^1$ to $R^5$ are independently hydrogen, deuterium, a cyano group, a halogen, a substituted or unsubstituted C1 to C4 alkyl group, a substituted or unsubstituted C6 to C10 aryl group, a substituted or unsubstituted C3 to C40 silyl group, or a combination thereof, at least one of $R^1$ to $R^5$ is a cyano group, halogen, a substituted or unsubstituted C1 to C4 alkyl group, a substituted or unsubstituted C6 to C10 aryl group, or a substituted or unsubstituted C3 to C40 silyl group, $X^6$ and $X^7$ are independently $CR^aR^b$ or $SiR^cR^d$, $R^a$ to $R^d$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, $X^8$ to $X^{10}$ are independently N or CH, at least one of $X^8$ to $X^{10}$ is N, M is Ir, Os, Pt, Pb, Re, Ru, or Pd, m and n are independently an integer of 1 or 2, and m+n is an integer of 3, wherein the substituted refers to a substitution where at least one hydrogen is replaced by deuterium, a halogen, a hydroxy group, an amino group, a C1 to C30 amine group, a nitro group, a C3 to C40 silyl group, a C1 to C30 alkyl group, C1 to C10 alkylsilyl group, C3 to C30 cycloalkyl group, a C6 to C30 aryl group, a C1 to C20 alkoxy group, or a cyano group.

2. The compound of claim 1, wherein the Chemical Formula 1 is represented by one of Chemical Formulae 2 to 4:

[Chemical Formula 2]

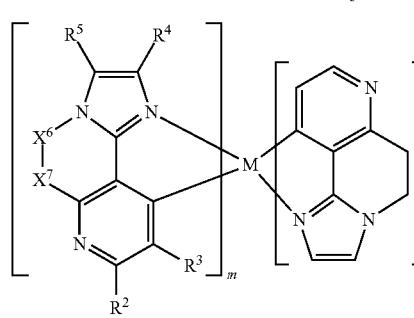

[Chemical Formula 3]

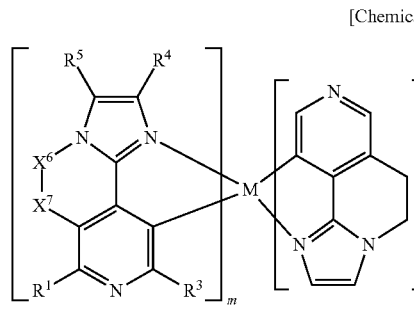

-continued

[Chemical Formula 4]

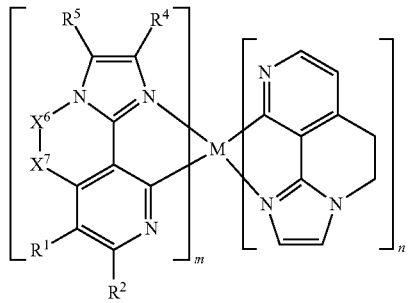

wherein, in Chemical Formulae 2 to 4, $R^1$ to $R^5$ are independently hydrogen, deuterium, a cyano group, a halogen, a substituted or unsubstituted C1 to C4 alkyl group, a substituted or unsubstituted C6 to C10 aryl group, a substituted or unsubstituted C3 to C40 silyl group, or a combination thereof, at least one of $R^1$ to $R^5$ is a cyano group, halogen, a substituted or unsubstituted C1 to C4 alkyl group, a substituted or unsubstituted C6 to C10 aryl group, a substituted or unsubstituted C3 to C40 silyl group, or a combination thereof, $X^6$ and $X^7$ are independently $CR^aR^b$ or $SiR^cR^d$, $R^a$ to $R^d$ are independently, hydrogen, deuterium, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 silyl group, halogen, a cyano group, a hydroxyl group, an amino group, a nitro group, a carboxyl group, or a combination thereof, M is Ir, Os, Pt, Pb, Re, Ru, or Pd, m and n are independently an integer of 1 or 2, and m+n is an integer of 3, wherein the substituted refers to a substitution where at least one hydrogen is replaced by deuterium, halogen, a hydroxy group, an amino group, a C1 to C30 amine group, a nitro group, a C3 to C40 silyl group, a C1 to C30 alkyl group, C1 to C10 alkylsilyl group, C3 to C30 cycloalkyl group, a C6 to C30 aryl group, a C1 to C20 alkoxy group, or a cyano group.

3. The compound of claim 1, wherein Chemical Formula 1 is represented by one of Chemical Formulae 5 to 7:

[Chemical Formula 5]

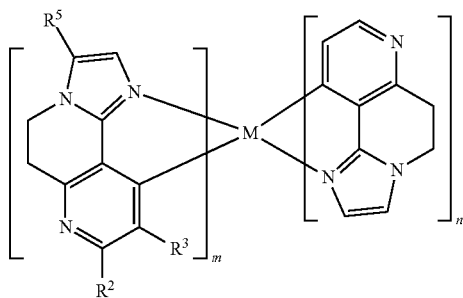

-continued

[Chemical Formula 6]

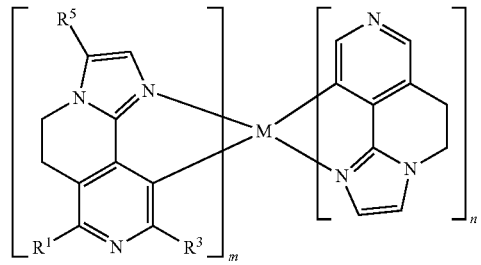

[Chemical Formula 7]

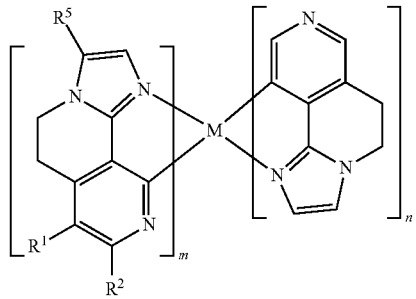

wherein, in Chemical Formulae 5 to 7, $R^1$ to $R^3$ and $R^5$ are independently hydrogen, deuterium, a cyano group, halogen, a substituted or unsubstituted C1 to C4 alkyl group, a substituted or unsubstituted C6 to C10 aryl group, a substituted or unsubstituted C1 to C40 silyl group, or a combination thereof, at least one of $R^1$ to $R^3$ and $R^5$ is a cyano group, halogen, a substituted or unsubstituted C1 to C4 alkyl group, a substituted or unsubstituted C6 to C10 aryl group, a substituted or unsubstituted C1 to C40 silyl group, or a combination thereof, M is Ir, Os, Pt, Pb, Re, Ru, or Pd, m and n are independently an integer of 1 or 2, and m+n is an integer of 3, wherein the substituted refers to a substitution where at least one hydrogen is replaced by deuterium, halogen, a hydroxy group, an amino group, a C1 to C30 amine group, a nitro group, a C3 to C40 silyl group, a C1 to C30 alkyl group, a C1 to C10 alkylsilyl group, a C3 to C30 cycloalkyl group, a C6 to C30 aryl group, a C1 to C20 alkoxy group, or a cyano group.

4. The compound of claim 1, wherein the $R^1$ to $R^5$ are independently hydrogen, deuterium, a cyano group, a halogen, a substituted or unsubstituted C1 to C4 alkyl group, a substituted or unsubstituted C6 to C10 aryl group, a substituted or unsubstituted C3 to C40 silyl group, or a combination thereof, and at least one of $R^1$ to $R^5$ is a cyano group, a methyl group, an ethyl group, an isopropyl group, a t-butyl group, a trimethylsilyl group, a fluorine group, a trifluoromethyl group, or a phenyl group.

5. The compound of claim 1, wherein the Chemical Formula 1 is one of compounds of Group 1:
[Group 1]
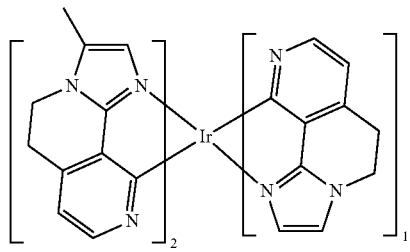
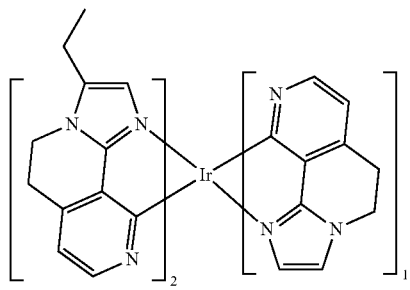
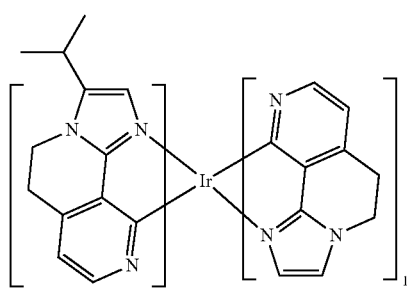
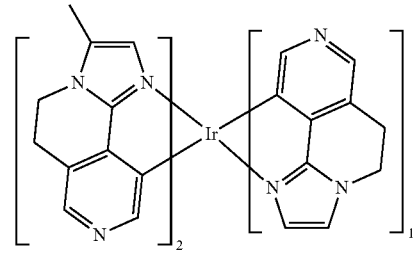
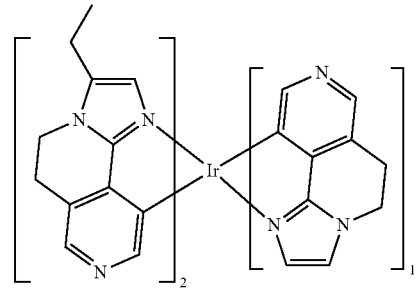
-continued
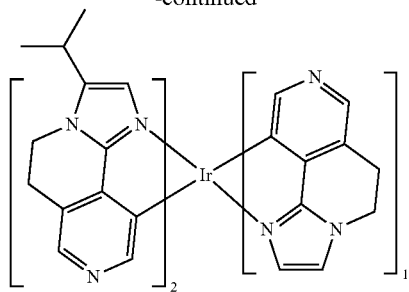
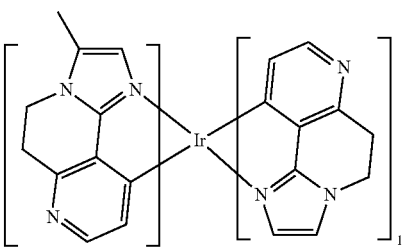
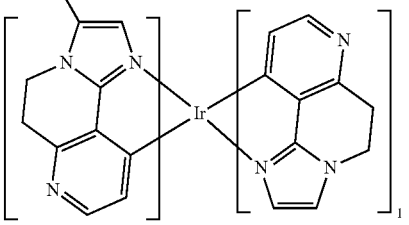
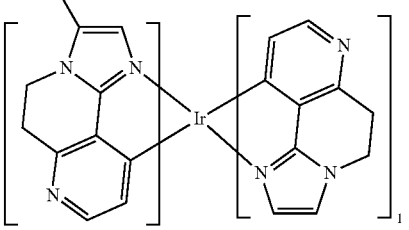
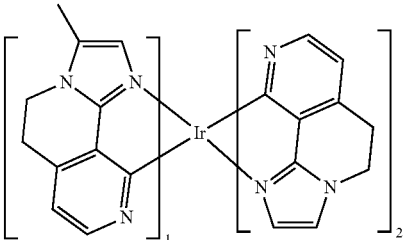
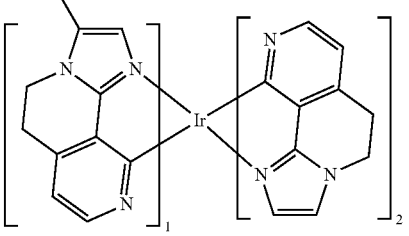

-continued
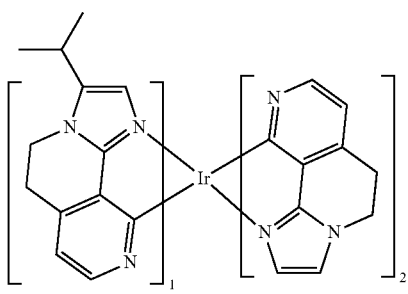
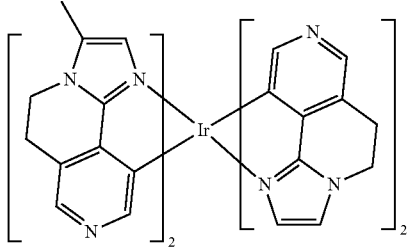
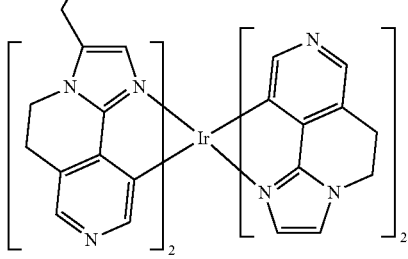
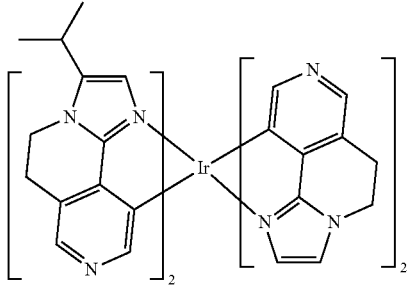
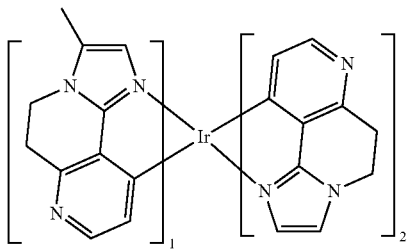
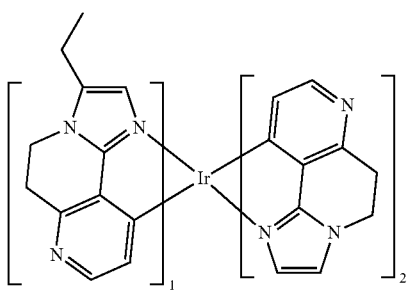
-continued
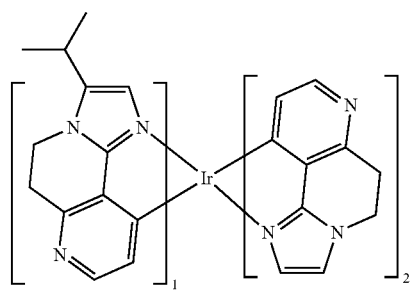
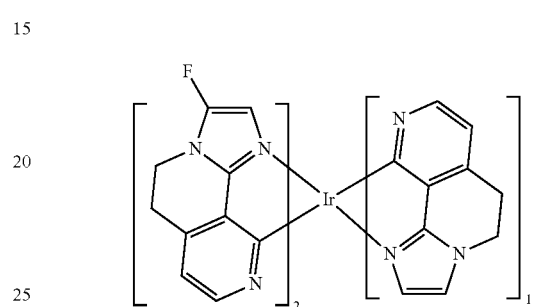
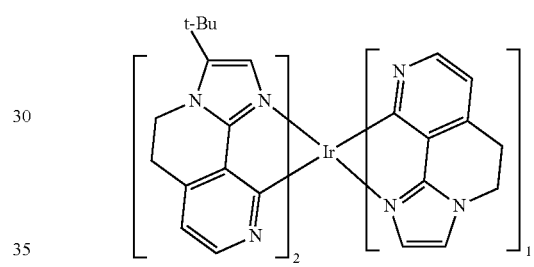
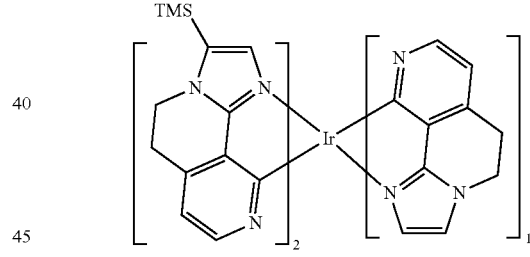
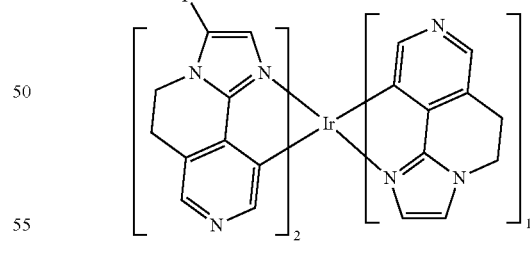
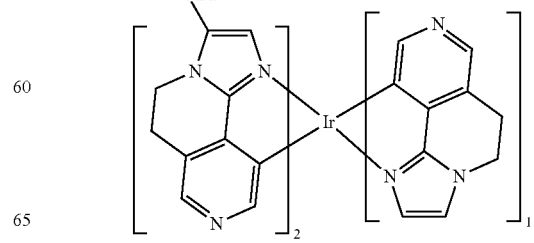

51
-continued
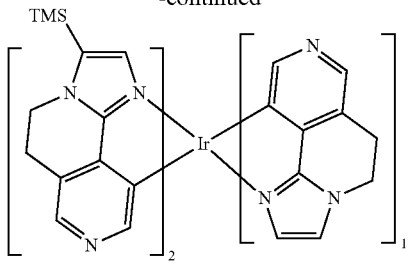
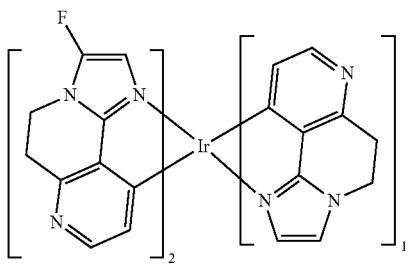
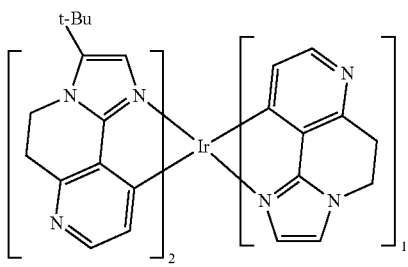
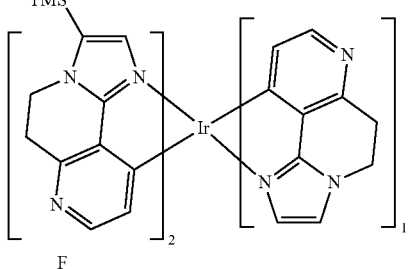
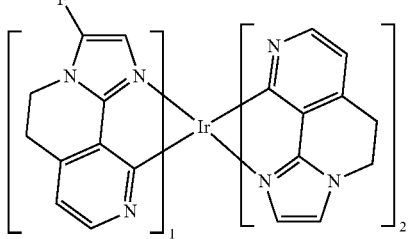
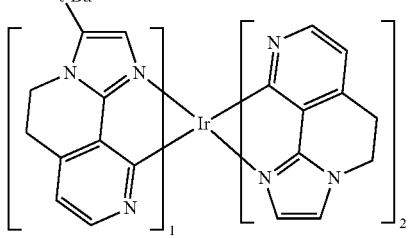
52
-continued
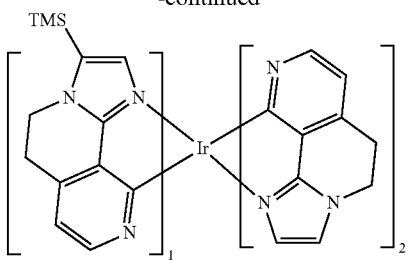
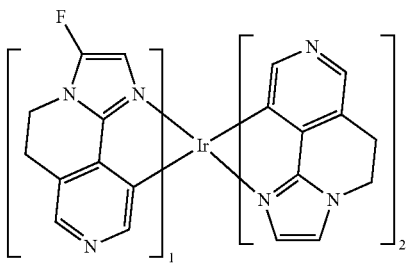
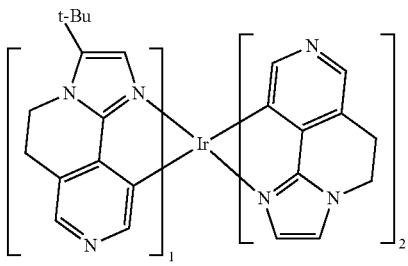
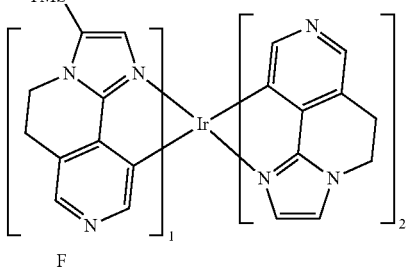
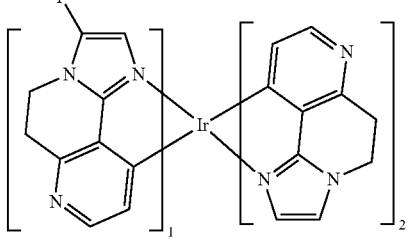
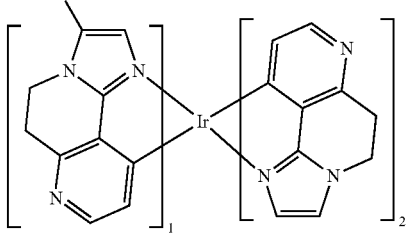

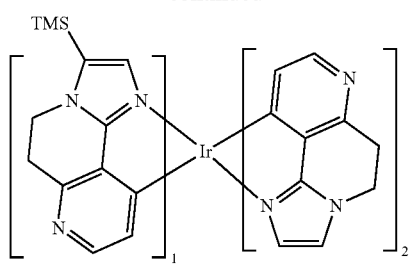
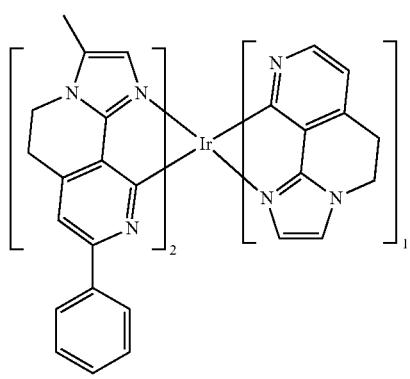
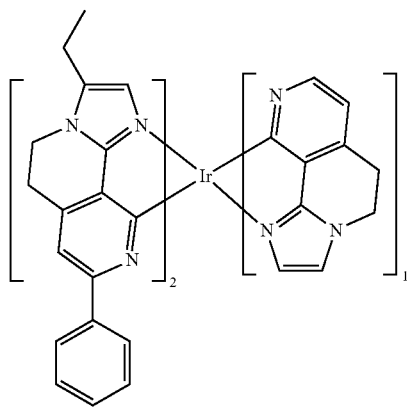
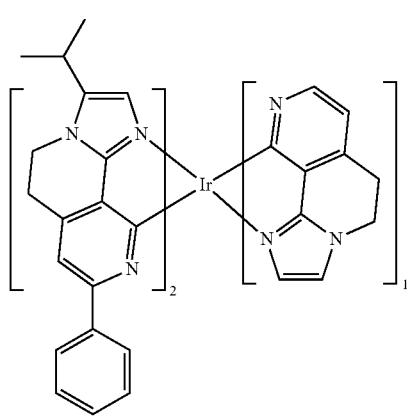
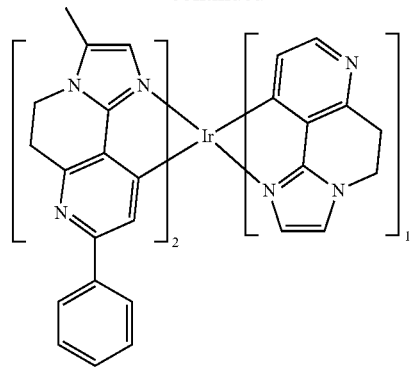
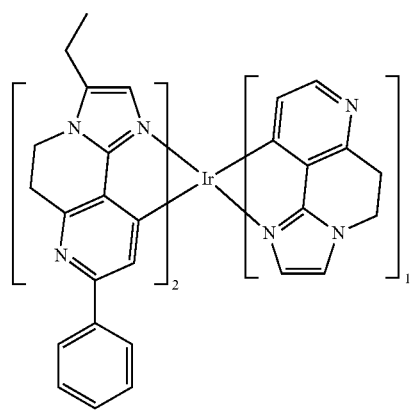
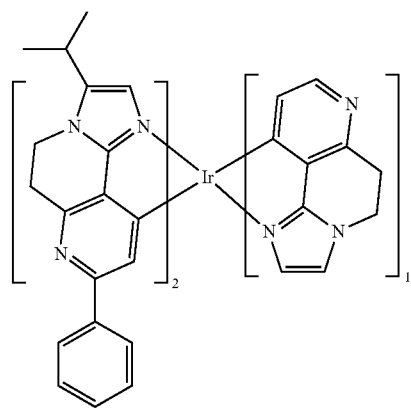
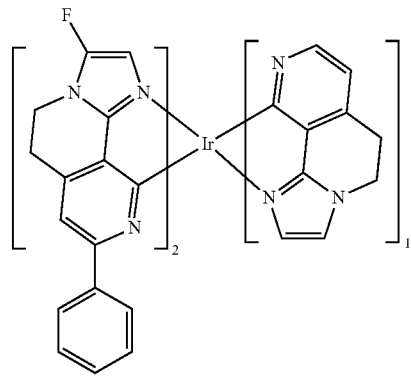

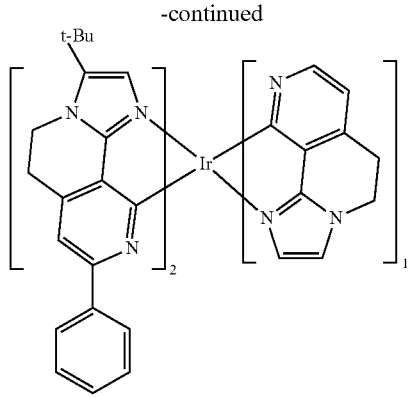
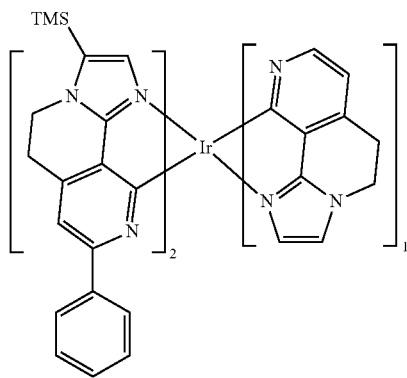
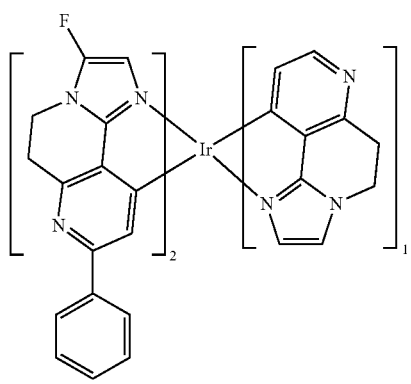
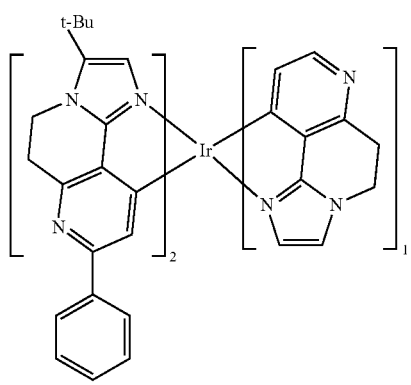
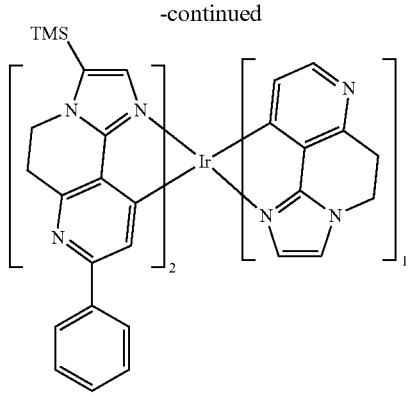
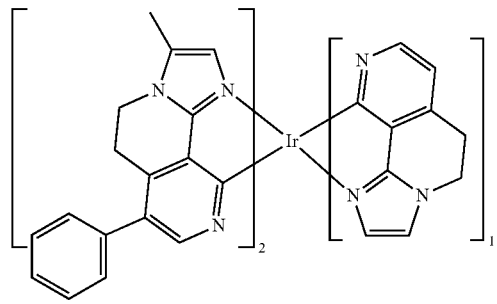
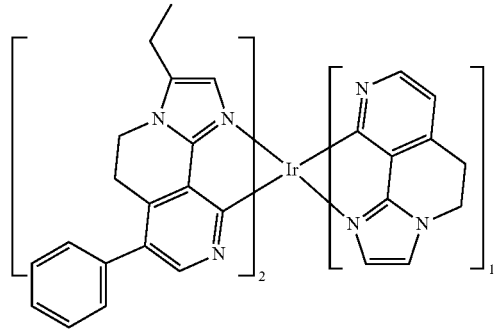
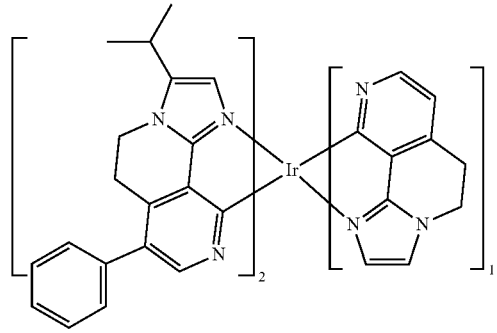
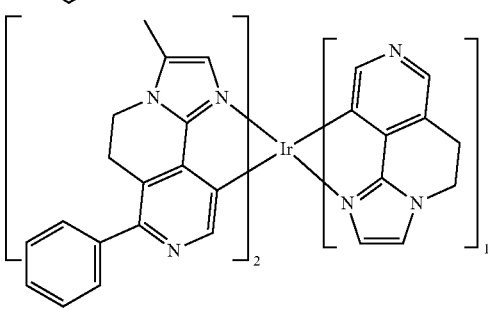

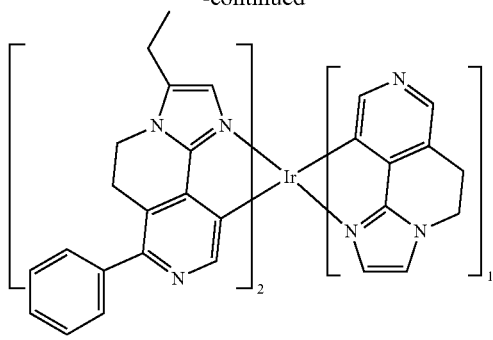
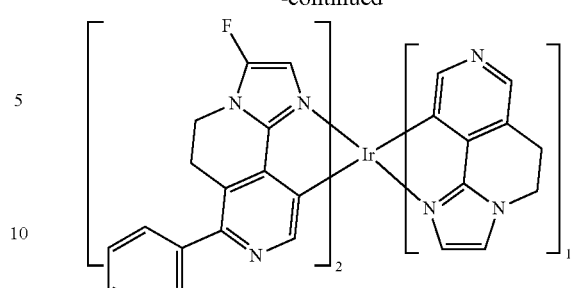
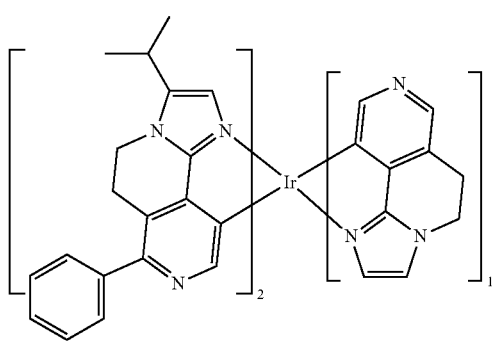
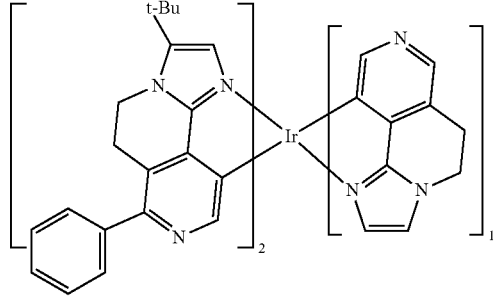
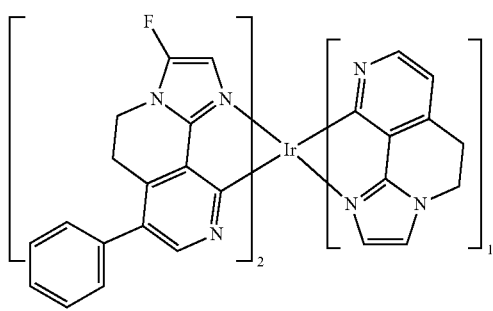
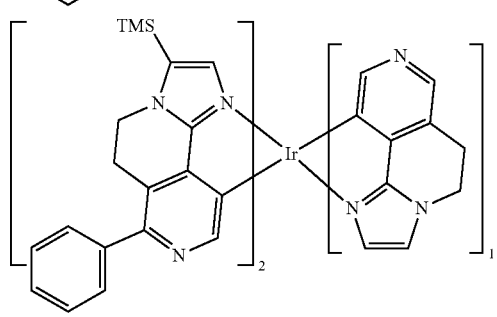
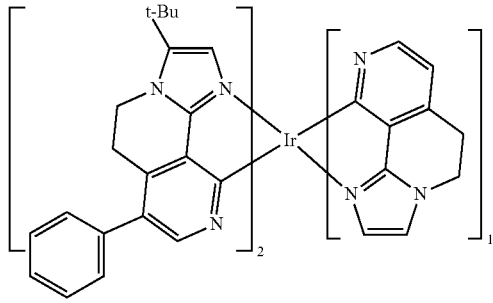
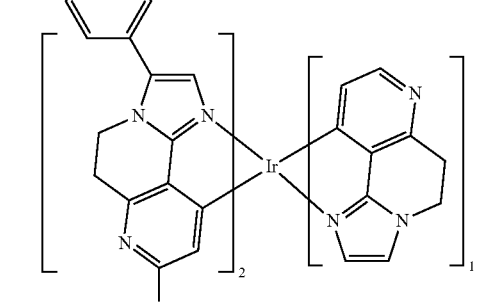
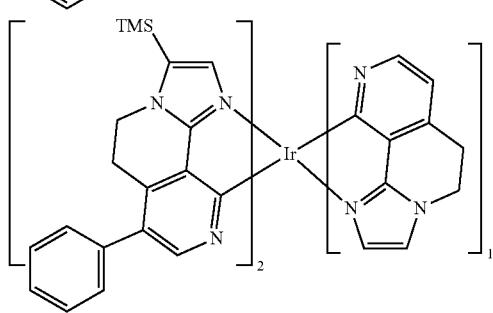
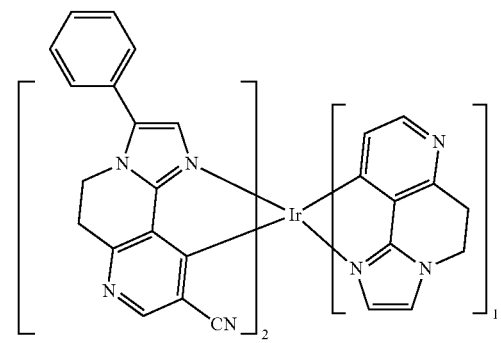

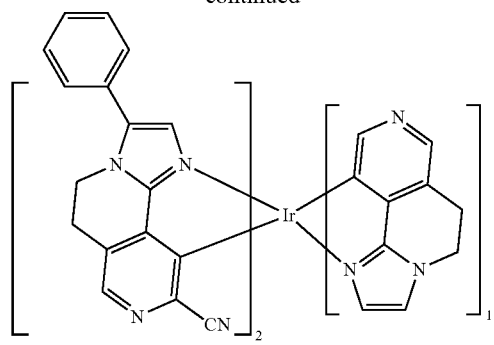
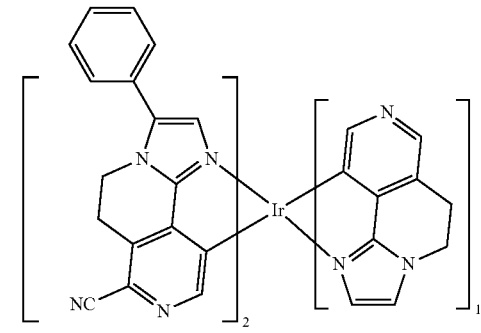
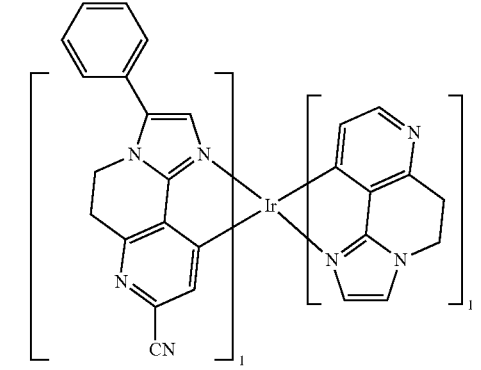
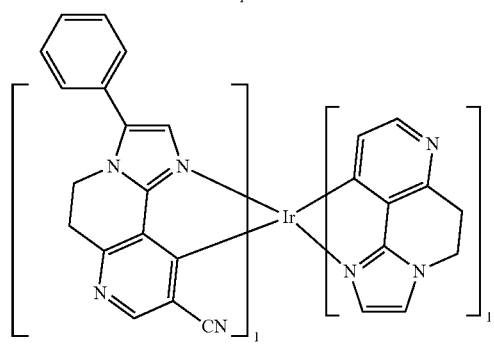
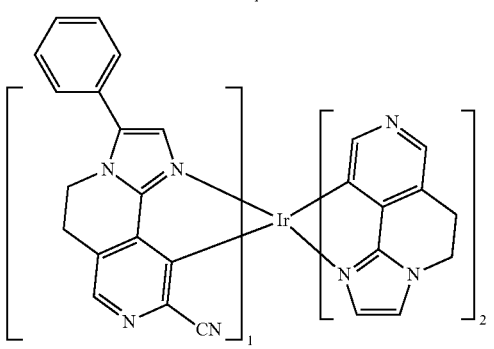
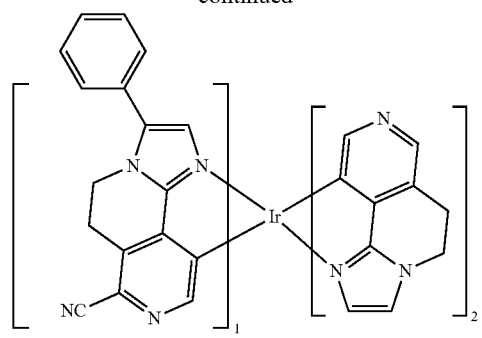
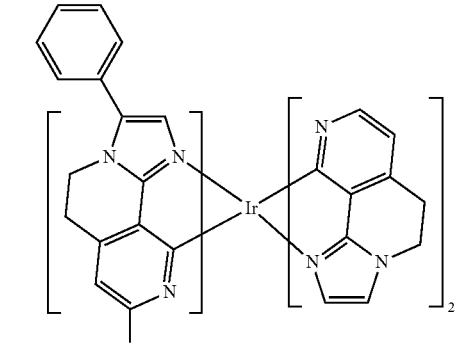
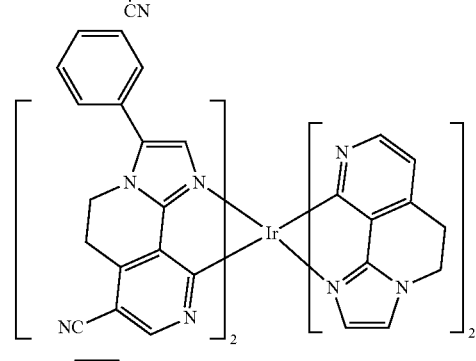
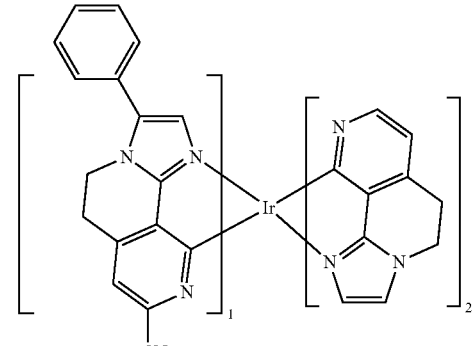
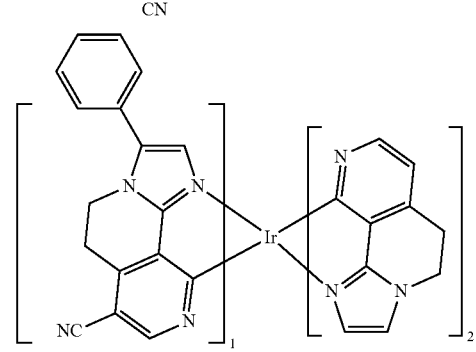

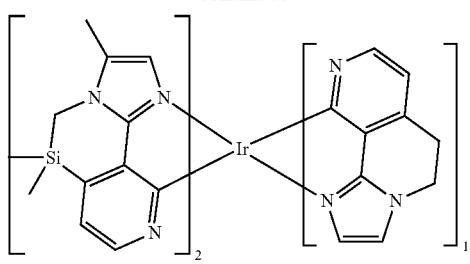
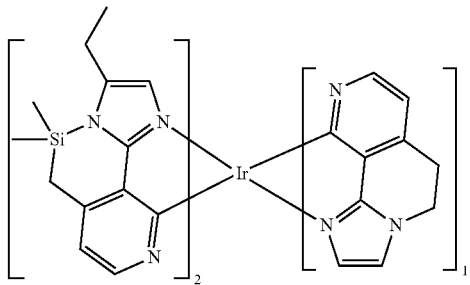
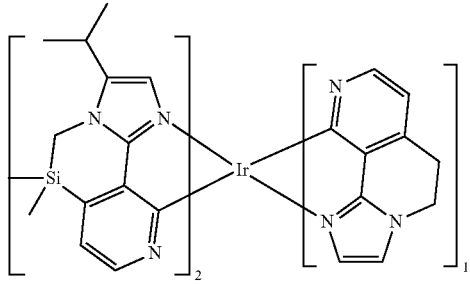
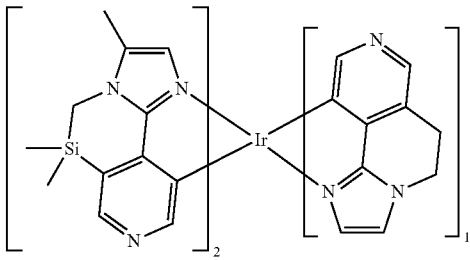
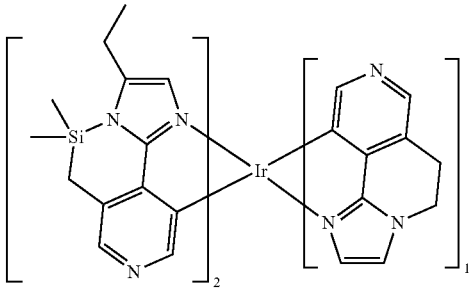
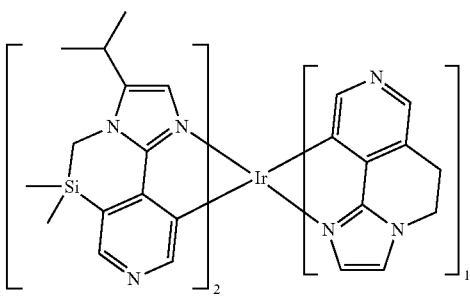
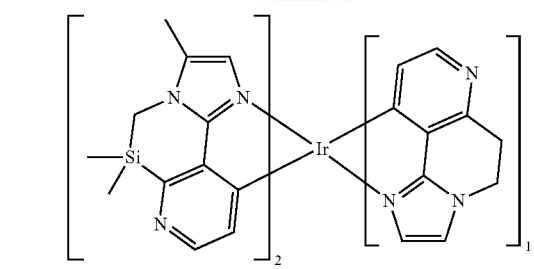
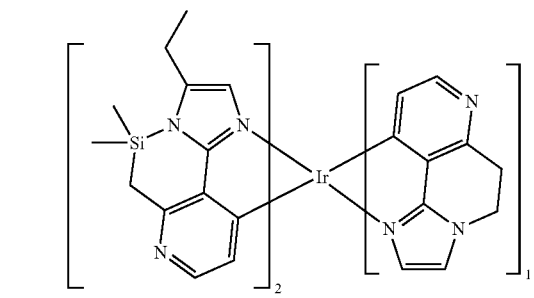
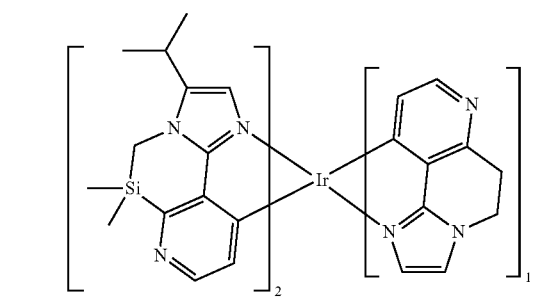
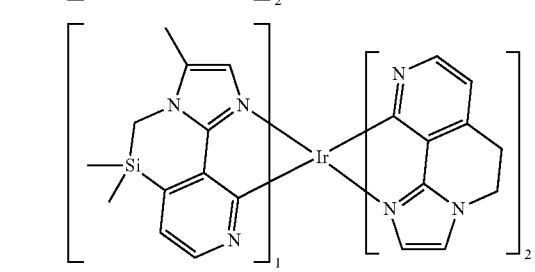
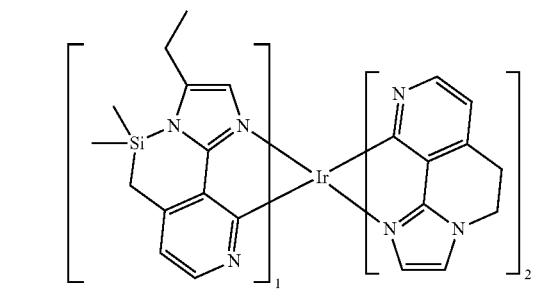
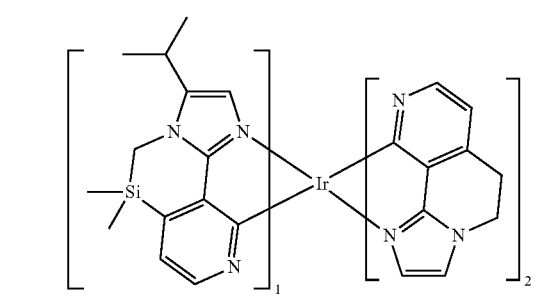

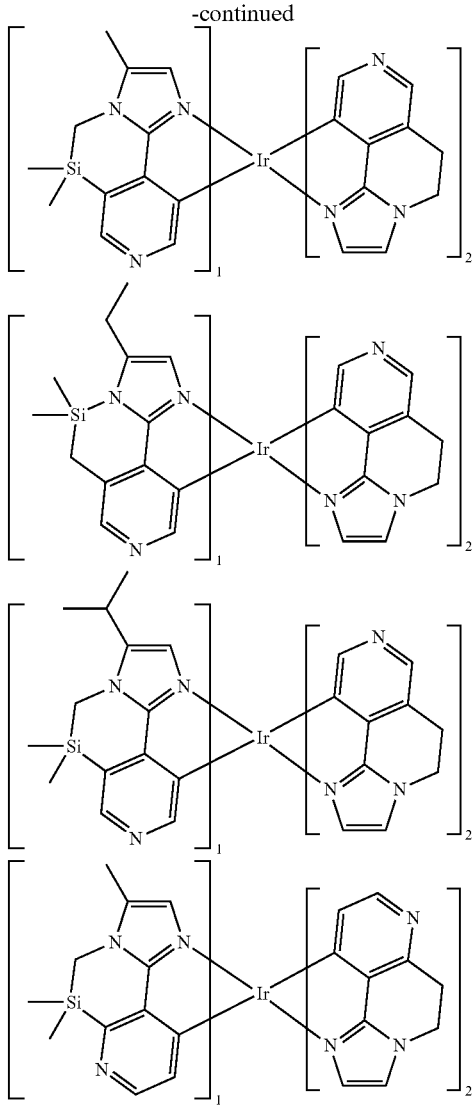

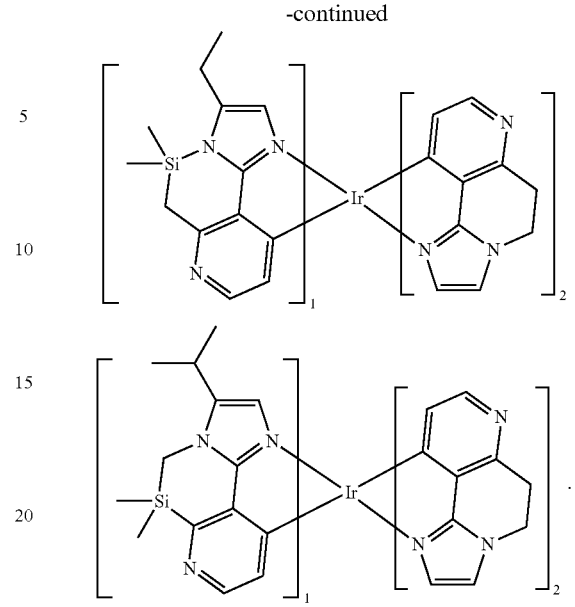

6. The compound of claim 1, wherein the compound is used for an organic optoelectronic device.

7. An organic optoelectronic device comprising
an anode and a cathode facing each other and
one layered organic layer between the anode and the cathode, wherein the organic layer includes the compound of claim 1.

8. The organic optoelectronic device of claim 7, wherein the organic layer comprises an emission layer, and
the emission layer comprises the compound.

9. The organic optoelectronic device of claim 8, wherein the compound is included as a dopant of the emission layer.

10. A display device comprising the organic optoelectronic device of claim 7.

* * * * *